United States Patent
Hettrick et al.

(10) Patent No.: US 12,064,226 B2
(45) Date of Patent: *Aug. 20, 2024

(54) SYSTEMS AND METHODS FOR EVALUATING NEUROMODULATION THERAPY VIA HEMODYNAMIC RESPONSES

(71) Applicant: Medtronic Ireland Manufacturing Unlimited Company, Dublin (IE)

(72) Inventors: Douglas Hettrick, Andover, MN (US); Avram Scheiner, Vadnais Heights, MN (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 180 days.

This patent is subject to a terminal disclaimer.

(21) Appl. No.: 17/724,906

(22) Filed: Apr. 20, 2022

(65) Prior Publication Data
US 2022/0240807 A1   Aug. 4, 2022

Related U.S. Application Data

(60) Continuation of application No. 16/451,395, filed on Jun. 25, 2019, now Pat. No. 11,311,205, which is a (Continued)

(51) Int. Cl.
*A61B 18/12* (2006.01)
*A61B 5/00* (2006.01)
(Continued)

(52) U.S. Cl.
CPC .......... *A61B 5/0538* (2013.01); *A61B 5/4848* (2013.01); *A61B 18/1206* (2013.01);
(Continued)

(58) Field of Classification Search
CPC ... A61B 5/4848; A61B 5/0538; A61B 5/4052; A61B 5/6859; A61B 2018/00511;
(Continued)

(56) References Cited

U.S. PATENT DOCUMENTS

| 10,368,775 B2 * | 8/2019 | Hettrick | A61B 5/0538 |
| 2012/0296232 A1 * | 11/2012 | Ng | A61B 18/1492 600/554 |

(Continued)

*Primary Examiner* — Sean W Collins
(74) *Attorney, Agent, or Firm* — Shumaker & Sieffert, P.A

(57) ABSTRACT

Systems and methods for evaluating neuromodulation via hemodynamic responses are disclosed herein. A system configured in accordance with embodiments of the present technology can include, for example, a neuromodulation catheter comprising an elongated shaft having a distal portion, and a plurality of electrodes spaced along a distal portion. The system can further include a controller communicatively coupled to the electrodes. The controller can be configured to apply first and second stimuli at and/or proximate to a target site within a blood vessel before and after delivering neuromodulation energy to the target site, and detect, via at least one of the electrodes, vessel impedance resulting from the first and second stimuli to determine a baseline impedance and a post-neuromodulation impedance. The controller can further be configured to assess the efficacy of the neuromodulation based, at least in part, on a comparison of the baseline impedance and the post-neuromodulation impedance.

25 Claims, 11 Drawing Sheets

Related U.S. Application Data division of application No. 14/872,203, filed on Oct. 1, 2015, now Pat. No. 10,368,775.

(60) Provisional application No. 62/058,420, filed on Oct. 1, 2014, provisional application No. 62/058,434, filed on Oct. 1, 2014.

(51) Int. Cl.
*A61B 5/0538* (2021.01)
*A61B 18/14* (2006.01)
*A61M 25/00* (2006.01)
*A61B 18/00* (2006.01)
*A61N 1/05* (2006.01)

(52) U.S. Cl.
CPC ..... *A61B 18/1492* (2013.01); *A61M 25/0043* (2013.01); *A61B 2018/00404* (2013.01); *A61B 2018/00434* (2013.01); *A61B 2018/00511* (2013.01); *A61B 2018/00577* (2013.01); *A61B 2018/00666* (2013.01); *A61B 2018/00875* (2013.01); *A61N 1/05* (2013.01)

(58) Field of Classification Search
CPC ............ A61B 18/1206; A61B 18/1492; A61B 2018/00875; A61B 2018/00577; A61B 2018/00666; A61B 2018/00404; A61B 2018/00434; A61M 25/0043; A61N 1/05
See application file for complete search history.

(56) References Cited

U.S. PATENT DOCUMENTS

| | | | |
|---|---|---|---|
| 2014/0012242 A1* | 1/2014 | Lee | A61B 18/02 606/21 |
| 2014/0128865 A1* | 5/2014 | Gross | A61N 1/36114 606/41 |
| 2017/0056104 A1* | 3/2017 | Asirvatham | A61B 18/1492 |

\* cited by examiner

SYSTEMS AND METHODS FOR EVALUATING NEUROMODULATION THERAPY VIA HEMODYNAMIC RESPONSES

CROSS-REFERENCE TO RELATED APPLICATION(S)

This application is continuation of U.S. patent application Ser. No. 16/451,395, filed Jun. 25, 2019, which is a divisional of U.S. patent application Ser. No. 14/872,203, filed Oct. 1, 2015, now U.S. Pat. No. 10,368,775, which claims the benefit of U.S. Provisional Patent Application Nos. 62/058,420 filed Oct. 1, 2014, and 62/058,434, filed Oct. 1, 2014, all of which are incorporated herein by reference in their entireties.

TECHNICAL FIELD

The present technology is related to neuromodulation. In particular, various embodiments of the present technology are related to systems and methods for assessing the efficacy of neuromodulation therapy via hemodynamic responses to stimuli.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Systems and methods in accordance with embodiments of the present technology can be configured to detect hemodynamic responses to stimuli before and after neuromodulation therapy. This information can be used to assess the efficacy of neuromodulation therapy in substantially real time during neuromodulation procedures. Specific details of several embodiments of the present technology are described herein with reference to FIGS. 1-13. Although many of the embodiments are described with respect to devices, systems, and methods for intravascular renal neuromodulation, other applications and other embodiments in addition to those described herein are within the scope of the present technology. For example, at least some embodiments of the present technology may be useful for intraluminal neuromodulation, for extravascular neuromodulation, for non-renal neuromodulation, and/or for use in therapies other than neuromodulation. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation device). The terms, "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

I. SELECTED EMBODIMENTS OF CATHETERS AND SYSTEMS FOR EVALUATING NEUROMODULATION THERAPY AND ASSOCIATED METHODS

Figure 1A:
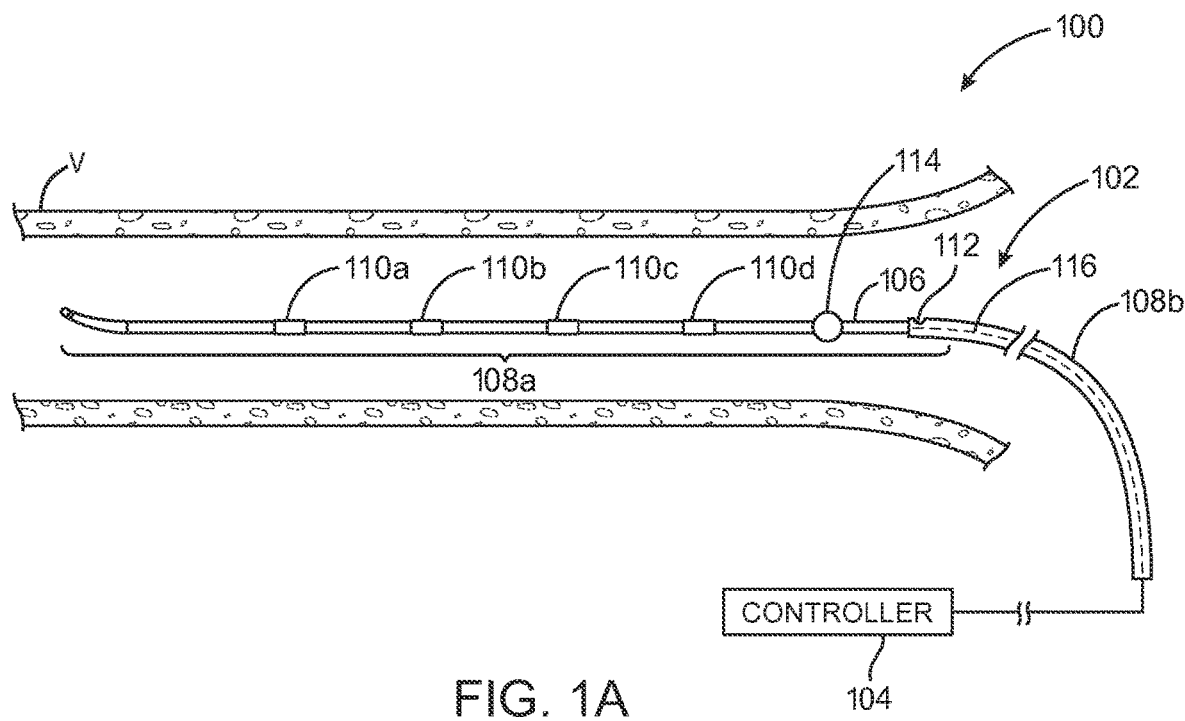
FIGS. 1A and 1B are partially schematic side views of a neuromodulation/evaluation system with a distal portion of a neuromodulation catheter in a first state and a second state, respectively, within a blood vessel of a human patient in accordance with an embodiment of the present technology.
Figure 1B:
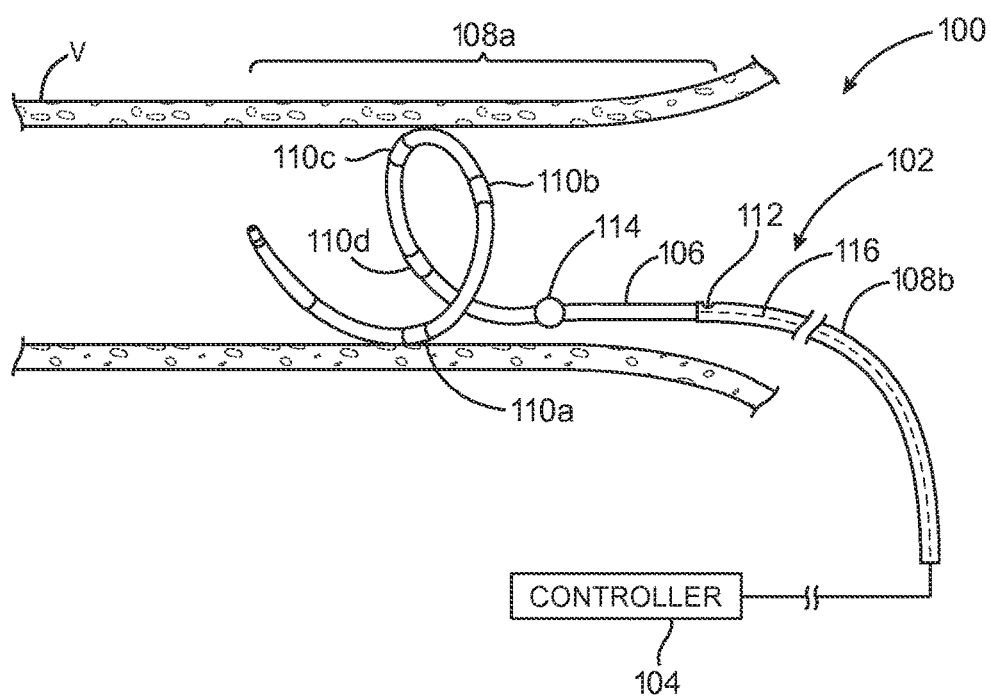

FIGS. 1A and 1B are partially schematic side views of a system 100 for applying and evaluating neuromodulation therapy ("system 100") configured in accordance with an embodiment of the present technology. The system 100 includes a neuromodulation catheter 102 and a controller 104 communicatively coupled to the neuromodulation catheter 102 via a wired or wireless communication link. In FIG. 1A, the neuromodulation catheter 102 is in a first state or arrangement in which a distal portion of the neuromodulation catheter 102 is at least generally straight along a portion of a blood vessel V. In FIG. 1B, the neuromodulation catheter 102 is in a second state or arrangement in which the distal portion of the neuromodulation catheter 102 is transformed or otherwise expanded to a spiral/helical shape.

As shown in FIGS. 1A and 1B, the neuromodulation catheter 102 includes an elongated shaft 106 having a distal portion 108a configured to be positioned at a target site within a blood vessel of a human patient (e.g., a renal artery) and a proximal portion 108b that extends outside of the patient to a handle (not shown) or other feature that allows an operator (not shown) to manipulate the distal portion 108a of the shaft 106. The neuromodulation catheter 102 also includes a plurality of energy delivery elements, such as electrodes (identified individually as first through fourth electrodes 110a-110d, respectively, and referred to collectively as electrodes 110) spaced along the distal portion 108a of the shaft 106. In the illustrated embodiment, the neuromodulation catheter 102 includes four electrodes 110. In other embodiments, however, the neuromodulation catheter 102 may include one, two, three, or more than four electrodes 110, and/or may include different energy delivery elements.

When positioned within the vessel V, the electrodes 110 and/or another type of energy delivery element can deliver neuromodulation energy to the target site to modulate or ablate nerves (e.g., renal nerves) proximate to the target site. The electrodes 110 and/or other features at the distal portion 108a of the shaft 106 can further be configured to apply stimuli at and/or proximate to the target site before and/or after neuromodulation, and detect a hemodynamic response caused by the stimuli. Stimuli, as used herein, refers to stimulations that are sufficient to evoke a neural response in nerves proximate to the vessel V (e.g., renal nerves), but not so great that they permanently affect neural functions. The stimuli can be applied proximal to the site of neuromodulation, distal to the site of neuromodulation, and/or on either side of the neuromodulation site. For example, in certain embodiments the stimuli is applied at the ostium of a vessel (e.g., the ostium of the renal artery). In other embodiments, however, the stimuli may be applied at other suitable locations.

It is expected that a successful or effective neuromodulation treatment or therapy (i.e., when nerves are ablated to a desired degree) causes a hemodynamic response, which can be reflected by a local change in hemodynamics and/or a global change in hemodynamics. Local changes in hemodynamics can be characterized by hemodynamic responses caused by efferent nerve activity, whereas global changes in hemodynamics can be characterized by hemodynamic responses caused by afferent nerve activity. Changes in hemodynamics, such as changes in vessel diameter, can be detected as a result of successful denervation without the application of a stimulus. For example, the diameter, cross-sectional area, or segmental volume of a vessel can be measured immediately before and after neuromodulation therapy. Increases in the vessel dimension (e.g., an increase in vessel diameter) after neuromodulation therapy may be indicative of a successful neuromodulation treatment because the modulation or ablation of the efferent nerves is expected to cause an immediate decrease or removal sympathetically induced vasoconstriction, causing a decrease in vessel tone and dilating the vessel. In addition or alternatively, a hemodynamic response can be measured by stimulating nerves at or proximate to the neuromodulation site before and after neuromodulation therapy, and detecting a change in hemodynamic response caused by each stimulus. For example, an electrical or pharmaceutical stimulus can be applied to a vessel to stimulate the nerves at or proximate to the target site. When the nerves are functioning (i.e., conducting signals), the afferent nerves will respond to the stimulus and cause a hemodynamic response. This hemodynamic response can be measured by detecting changes in vessel dimension (e.g., diameter, cross-sectional area, and segmental volume), pressure within the vessel, blow flow through the vessel, heart rate, and/or other parameters indicative of a hemodynamic response. It is expected that the hemodynamic response to the stimulus will be eliminated or at least lessened after the nerves have been effectively ablated to a desired degree because the afferent nerves have been ablated or modulated. Accordingly, comparing the hemodynamic responses before and after neuromodulation is expected to indicate whether a neuromodulation treatment is successful. In certain embodiments, vessel dimensions or other hemodynamic parameters can be measured before and after neuromodulation therapy (without stimulation) to determine the efficacy of the neuromodulation treatment on efferent nerves proximate to the vessel, and also measured before and after neuromodulation therapy as a response to stimuli to determine the efficacy of the neuromodulation treatment on afferent nerves.

In certain embodiments, the electrodes 110 can be configured to: (1) apply stimuli to the vessel V, and (2) detect/measure changes in vessel impedance caused by the stimuli, which can be correlated to changes in vessel diameter. As will be appreciated by those skilled in the art, blood is more conductive than vessel tissue and, therefore, vessel impedance is lower when the vessel has a larger diameter (i.e., when more blood is contained in the vessel) and higher when the vessel has a smaller diameter (i.e., when less blood is contained in the vessel). Accordingly, when the electrodes 110 are positioned in the vessel, impedance measurements taken by the electrode(s) 110 in response to the stimuli can be correlated to changes in vessel diameter, segmental volume, and/or cross-sectional area (i.e., a hemodynamic response), and used to assess the efficacy of the neuromodulation treatment. As discussed above, the neuromodulation procedure itself may cause immediate dilation of the vessel V (e.g., the renal artery) due to immediate removal of sympathetically induced vasoconstriction. Thus, one or more of the electrodes 110 can be used to measure a segmental volume of the vessel V, a cross-sectional area of the vessel V, and/or a vessel diameter just before and after neuromodulation (i.e., ablation), and these measurements may indicate an immediate dilation of the vessel V and a successful therapeutic result. In certain embodiments, these parameters can be determined using quadripolar impedance measurements, which are detected by applying a substantially homogeneous electric field across the electrodes 110 (e.g., generated by the first and fourth electrodes 110a and 110d) to allow for accurate impedance measurements (e.g., detected by the second and third electrodes 110b and 110c).

As shown in FIG. 1A, the distal portion 108a of the shaft 106 can be positioned along a portion of the vessel V in a substantially straight configuration. One or more of the electrodes 110 can be used to detect a baseline impedance measurement before neuromodulation energy is applied to the target site. For example, the initial impedance of the vessel V can be detected across the second and third electrodes 110b and 110c (i.e., the inner two electrodes), and this initial impedance can be correlated to the vessel diameter, vessel area, and/or vessel volume (e.g., via the controller 104) using the cylindrical equation described by Baan and/or using known physical relationships between impedance and vessel dimensions (e.g., as described in Hettrick D A, Battocletti J, Ackmann J, Linehan J, Warltier D C. In vivo measurement of real-time aortic segmental volume using the conductance catheter, *Ann Biomed Eng.* 1998; 26(3):431-40). By these known physical relationships, a relative change in mean impedance or impedance pulse width is expected to indicate a proportionate relative change in local vessel diameter, vessel area, and/or vessel volume.

The controller 104 can then send signals to the first and fourth electrodes 110a and 110d (i.e., the outer electrodes) to apply an electrical stimulus across the target site to stimulate the nerves proximate to the vessel V, and the second and third electrodes 110b and 110c can detect the impedance of the vessel V resulting from the stimulus. The electrical stimulation applied by the electrodes 110 is sufficient to stimulate the autonomic nerves proximate to the vessel V, which is expected to cause vessel contraction. For example, when the neuromodulation catheter 102 is in the renal artery, the electrical stimulation may have a frequency of about 10-30 Hz (e.g., 20 Hz), a pulse duration of 5-10 ms, an amplitude of 15-20 V, and be applied for 1-3 minutes. In other embodiments, however, the electrical stimulation may have different parameters depending upon the placement of the neuromodulation catheter 102 and the position of the nerves sought to be stimulated.

The controller 104 and/or another feature can subtract the initial vessel impedance from the impedance measured after stimulation to determine a change in pre-neuromodulation, baseline impedance. The controller 104 can also (or alternatively) convert the baseline impedance values (taken before and after stimulation) to vessel diameters, and take the difference of the two to determine a baseline change in vessel diameter.

After determining the baseline vessel impedance/diameter, the distal portion 108a of the shaft 106 can then be transformed into the spiral/helical shape shown in FIG. 1B such that at least one of the electrodes 110 makes contact with the vessel wall. The dimensions (e.g., outer diameter and length) of the spiral/helical portion of the shaft 106 can be selected to accommodate the vessels or other body lumens in which the distal portion of the catheter 102 is designed to be delivered. For example, the axial length of the spiral/helical portion of the shaft 106 may be selected to be no longer than a patient's renal artery (e.g., typically less than 7 cm), and have a diameter that accommodates the inner diameter of a typical renal artery (e.g., about 2-10 mm). In other embodiments, the spiral/helical portion of the shaft 106 can have other dimensions depending on the body lumen within which it is configured to be deployed. In further embodiments, the distal portion 108a of the shaft 106 can have other suitable shapes (e.g., semi-circular, curved, straight, etc.), and/or the neuromodulation catheter 102 can include multiple support members configured to carry one or more electrodes 110. The distal portion 108a of the shaft 106 may also be designed to apply a desired outward radial force to a vessel when expanded to the spiral/helical deployed state (shown in FIG. 1B) to place one or more of the electrodes 110 in contact with the vessel wall. For example, FIG. 1B illustrates the distal portion 108a of the shaft 106 in a deployed state with the electrodes 110 in apposition with the interior wall of the vessel V.

One or more of the electrodes 110 can apply radio frequency (RF) energy (e.g., monopolar and/or bipolar RF energy) to the vessel V to ablate the nerves proximate to the vessel wall. In certain embodiments, the same electrodes 110 can be used to apply stimulation and ablation energy, as well as measure impedance of the vessel V. In other embodiments, the neuromodulation catheter 102 can include electrodes, transducers, or other elements to delivery energy to modulate nerves using other suitable neuromodulation modalities, such as pulsed electrical energy, microwave energy, optical energy, ultrasound energy (e.g., intravascularly delivered ultrasound, extracorporeal ultrasound, and/or high-intensity focused ultrasound (HIFU)), direct heat energy, radiation (e.g., infrared, visible, and/or gamma radiation), and/or other suitable types of energy. In certain embodiments, the neuromodulation catheter 102 may be configured for cryotherapeutic treatment, and can apply cryogenic cooling to the vessel V with a refrigerant (e.g., via a balloon catheter that circulates the refrigerant). In still other embodiments, the neuromodulation catheter 102 is configured for chemical-based treatment (e.g., drug infusion), and the neuromodulation catheter 102 can apply one or more chemicals to the treatment site to effectuate neuromodulation. Such chemicals can include neurotoxins, antagonists (e.g., guanethadine), and/or tissue necrosis-inducing agents (e.g., ethyl alcohol). In such embodiments, the mode of neuromodulation (e.g., RF, ultrasound, chemical ablation, cryo-ablation) may differ from the mode of stimulation (e.g., electrical or chemical stimulation).

After neuromodulation energy has been applied to the target site, the distal portion 108a of the shaft 106 can again be straightened as shown in FIG. 1A, and one or more of the electrodes 110 can be used to detect a post-neuromodulation vessel impedance or vessel diameter. For example, the impedance of the vessel V can be detected across the second and third electrodes 110b and 110c to determine a baseline vessel impedance or vessel diameter after neuromodulation. The neuromodulation treatment may change the baseline vessel impedance/diameter from the initial baseline impedance/diameter measured before neuromodulation energy is applied, and therefore measuring vessel impedance before a second stimulation allows any such change to be taken into account. After the baseline, post-neuromodulation vessel impedance/diameter has been determined, the controller 104 can send a signal to the first and fourth electrodes 110a and 110d to apply an electrical stimulus across the vessel V, and the second and third electrodes 110b and 110c can detect the resultant vessel impedance. The controller 104 can then take the difference of the changes in vessel impedances or vessel diameters detected before and after the post-neuromodulation stimulation to determine a post-neuromodulation vessel impedance or diameter.

In other embodiments, different electrodes and/or electrode configurations can be used to apply the pre- and post-neuromodulation stimuli and/or detect the pre- and post-neuromodulation vessel impedances. For example, one or more separate stimulation electrodes can be positioned along the shaft 106 proximal to the first through fourth electrodes 110a-110d, and designated to apply stimuli. The stimulation electrode(s) can be configured to be positioned at an ostium of the vessel V (e.g., the ostium of the renal artery), a desired position within the vessel V, on one or both sides of a neuromodulation site, proximal to the neuromodulation site, and/or at other suitable positions for neurostimulation. In further embodiments, the distal portion of the neuromodulation catheter 102 can be arranged in a different shape (other than substantially straight) while applying stimuli and/or detecting vessel impedance, as long as the electrodes 110 are in substantially the same configuration during the pre- and post-neuromodulation measurements to maintain consistency in the impedance measurements. For example, the distal portion 108a of the shaft 106 can be positioned along a portion of the vessel V and expanded into a helical configuration (e.g., as shown in FIG. 1B) such that a portion of at least one electrode 110 contacts the vessel wall and a portion of at least one electrode 110 is exposed to blood flow. The baseline, pre-neuromodulation impedance measurement, ablative therapy, and post-neuromodulation impedance measurement can then be performed in the same manner previously described, while the distal portion 108a remains in the expanded helical configuration. For example, the portions of the electrodes 110 contacting the vessel wall may apply ablative energy to the vessel, and the portions of the electrodes 110 exposed to blood flow through the vessel lumen may be used to measure vessel impedance. In further embodiments, the distal portion 108a of the shaft 106 can have other suitable configurations while measuring pre- and post-neuromodulation impedance and/or applying ablation energy. For example, the distal portion of the neuromodulation catheter 102 can place some of the electrodes 110 in contact with the vessel wall, while placing other electrodes 110 into positions exposed to blood flowing through the vessel V. Accordingly, various electrodes 110 may be in direct contact with the vessel wall, in partial contact with the vessel wall, or not in contact with the vessel wall.

The changes in post-neuromodulation and pre-neuromodulation vessel impedances and/or diameters can be compared to each other to determine the efficacy of the neuromodulation treatment. In various embodiments, this comparison can be performed automatically by the controller 104 and/or another feature of the system 100. If the nerves have been ablated to a desired degree, it is expected that the change in post-neuromodulation vessel impedance/diameter will be less than the change in pre-neuromodulation vessel impedance/diameter because the application of ablation energy has decreased or eliminated the neural response to stimuli. Accordingly, an effective ablation treatment can be characterized as any decrease in the change in post-neuromodulation vessel impedance/diameter, the complete elimination of a change in post-neuromodulation vessel impedance/diameter, or a predefined decrease in the change in post-neuromodulation vessel impedance/diameter. In other embodiments, the system 100 can be configured to measure pre- and post-neuromodulation vessel impedances after the pre- and post-neuromodulation stimuli, without measuring the vessel impedance before the stimuli are applied, and these two pre- and post-neuromodulation impedance values can be compared to each other to determine the efficacy of the neuromodulation.

In certain embodiments, the difference between the post- and pre-neuromodulation impedances or diameters can be compared to a threshold value. The threshold value, for example, can be an equivalent to a percentage decrease in the change in impedance or vessel diameter (e.g., 15% less, 20% less, 50% less, 100% less, etc.), a predefined impedance or diameter value associated with effective neuromodulation, and/or a value based on other factors associated with successful neuromodulation. If the difference is less than the threshold value, the operator can elect to apply one or more additional rounds of neuromodulation energy to the treatment site using the same energy level or a higher energy level, and subsequently detect the hemodynamic response (e.g., the change in vessel impedance or diameter) as described above. Alternatively or in addition, the operator can reposition the distal portion 108a of the shaft 106 along the vessel V to apply neuromodulation energy to a different treatment site and measure the hemodynamic response (e.g., vessel impedance or diameter) at that new treatment site.

In various embodiments, the controller 104 can include instructions to automatically determine the pre- and post-neuromodulation changes in the vessel impedance and/or vessel diameter, and compare these values to the threshold. The controller 104 can then provide the operator with an indication of whether the neuromodulation treatment ablated the nerves to the desired degree. For example, the controller 104 can have a display that visually indicates whether the treatment was successful, such as a textual display, an indicator light, and/or other suitable indicator. In certain embodiments, the controller 104 may further be configured to provide the user with instructions to the user as to recommended changes to the energy application (e.g., amplitude, frequency, duration, etc.) that may provide the desired nerve ablation. For example, if a first application of neuromodulation energy was not considered effective, the controller 104 may recommend applying a higher level of the neuromodulation energy and/or applying the neuromodulation energy for a longer period of time.

Accordingly, the system 100 is expected to provide clinicians with a real time indication of nerve damage to establish whether a successful neuromodulation treatment has occurred. Thus, clinicians do not need to wait until after the procedure to determine whether the treatment was effective. Any additional energy applications necessary to effectuate neuromodulation can be performed while the catheter 102 is still within the vessel V. Accordingly, the system 100 can facilitate efficient and effective neuromodulation treatments. In addition, the system 100 allows the same electrodes 110 to be used to apply stimulation, measure impedance, and apply neuromodulation energy.

In selected embodiments, the system 100 can employ a pharmacological stimulus, rather than an electrical stimulus, to stimulate nerves proximate to the vessel and initiate a hemodynamic response, such as vasodilation. For example, as shown in FIGS. 1A and 1B, the distal portion of the neuromodulation catheter 102 can optionally include an outlet 112 configured to provide an acute injection of a pharmacological agent that stimulates the vessel V or adjacent nerves to cause a hemodynamic response (e.g., vasodilation). In the illustrated embodiment, the outlet 112 is positioned proximal to the electrodes 110 so that the pharmacological agent can flow distally through the vessel toward the electrodes 110 after injection, but in other embodiments the outlet 112 can be positioned elsewhere along the catheter 102 (e.g., between electrodes 110 or distal to the electrodes). The outlet 112 can be in fluid communication with a lumen 116 that extends through the neuromodulation catheter 102 and connects to a reservoir (not shown) of the pharmacological agent. Suitable pharmacological agents can include vasodilators, such as adenosine, bradykinin, and/or papaverine.

The controller 104 can be configured to automatically inject the pharmacological agent via the outlet 112 before and after neuromodulation energy is applied, and one or more of the electrodes 110 can be used to measure the change in vessel impedance or vessel diameter. Alternatively, a clinician can manually inject the pharmacological agent. In further embodiments, the pharmacological stimulus can be delivered proximate to the treatment site using other suitable means. For example, a separate catheter can be used to inject the pharmacological agent, or the pharmacological agent can be injected via a needle into the vessel lumen, directly into the vessel wall, and/or into the surrounding tissue to target neural pathways. Similar to the electrical stimulus, the pharmacological stimulus causes a hemodynamic response (e.g., vessel dilation) that can be measured before and after the neuromodulation energy is applied and used to assess the efficacy of the neuromodulation treatment.

As further shown in FIGS. 1A and 1B, the neuromodulation catheter 102 can also include at least one sensor 114 (shown schematically) and/or other device configured to detect a hemodynamic response to assess the efficacy of a neuromodulation therapy. For example, the sensor 114 can be a flow sensor, such as a Doppler velocity sensor or an ultrasonic flow meter, that can detect blood flow through the vessel V in response to the pre- and post-neuromodulation stimuli. In other embodiments, the sensor 114 can be a pressure sensor that measures changes in pressure within the vessel V in response to the pre- and post-neuromodulation stimuli. In certain embodiments, the catheter 102 can further include a fluid-filled lumen (not shown) extending along a length of the catheter 102 and open to the vessel V, and the lumen can be coupled to a pressure transducer (not shown) that measures the pressure within the vessel V. Similar to vessel diameter, blood flow and vessel pressure are expected to change in response to a stimulus, and these changes are expected to occur to at least a lesser degree after neuromodulation than before neuromodulation. Therefore, the changes in blood flow and/or vessel pressure measurements caused by an electrical or pharmacological stimulus can be detected before and after neuromodulation and then compared to a threshold value to determine the efficacy of neuromodulation therapy. In other embodiments, the system 100 can include additional features that measure hemodynamic responses.

Figure 2:
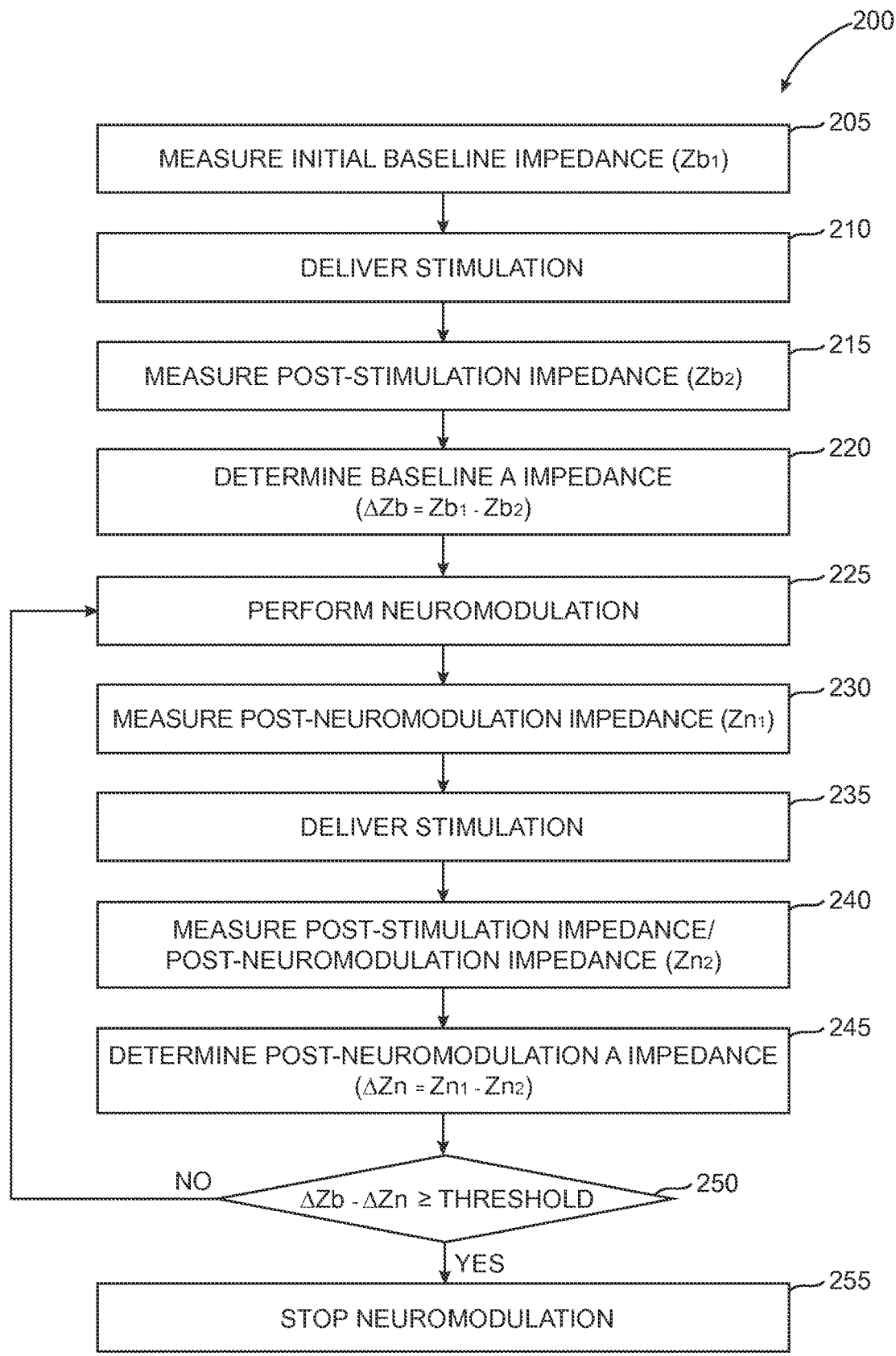
FIG. 2 is a block diagram illustrating a method of evaluating neuromodulation therapy in accordance with an embodiment of the present technology.

FIG. 2 is a block diagram illustrating a method 200 of evaluating neuromodulation therapy in accordance with an embodiment of the present technology. The method 200 can be implemented using the system 100 described above with reference to FIGS. 1A and 1B and/or other suitable systems for evaluating the efficacy of neuromodulation therapy. For example, the controller 104 and/or the catheter 102 can be used to perform the various steps of the method 200. As shown in FIG. 2, the method 200 includes measuring an initial baseline impedance ($Zb_1$) of a vessel (block 205). For example, as discussed with respect to FIG. 1A, a distal portion of a catheter can be positioned along within a vessel, and one or more electrodes on the catheter can be used to detect the initial pre-neuromodulation impedance ($Zb_1$) of the vessel. Stimulation can then be delivered at or near the target site (block 210), and the resultant post-stimulation baseline vessel impedance ($Zb_2$) can be measured (block 215). The stimulation can be electrical in nature and applied via one or more electrodes at the distal portion of the catheter. In other embodiments, however, the stimulation can be pharmacological and applied via an acute injection of a drug (e.g., a vasodilator) into the vessel or vessel wall. The post-stimulation baseline impedance ($Zb_2$) can be measured in a similar manner to the initial baseline impedance ($Zb_1$).

The method 200 continues by determining a change in the baseline impedance ($\Delta Zb$), which is the difference of the initial baseline impedance ($Zb_1$) and the post-stimulation baseline impedance ($Zb_2$) (block 220). In various embodiments, a controller can record the impedance measurements and include instructions to determine the baseline change in impedance ($\Delta Zb$). In certain embodiments, the initial and post-stimulation baseline impedance measurements ($Zb_1$) and ($Zb_2$) can be used to determine an initial baseline vessel diameter and a post-stimulation baseline vessel diameter, and the difference between the two diameters can be taken to determine a baseline change in vessel diameter.

The method 200 further continues by performing neuromodulation at the target site to ablate nerves proximate to the vessel wall (block 225). For example, the method 200 can include applying RF energy (e.g., via electrodes), pulsed electrical energy, microwave energy, optical energy, ultrasound energy (e.g., intravascularly delivered ultrasound, extracorporeal ultrasound, and/or HIFU), direct heat energy, radiation, cryogenic cooling, chemical-based treatment, and/or another suitable type of neuromodulation energy. The neuromodulation can be applied using the same catheter as is used for applying stimulation and measuring impedance, or a second catheter or other device can be used to perform neuromodulation.

The method 200 then measures post-neuromodulation vessel impedance ($Zn_1$) after neuromodulation has been applied (block 230), delivers stimulation (e.g., electrical and/or pharmacological) at or proximate to the target site (block 235), and measures post-stimulation, post-neuromodulation impedance ($Zn_2$) resulting from the stimulus (block 240). The controller and/or another device can then determine the difference between the post-neuromodulation, pre-stimulation impedance ($Zn_1$) and the post-neuromodulation, post-stimulation impedance ($Zn_2$) to provide a post-neuromodulation change in impedance ($\Delta Zn$) (block 245). In other embodiments, the controller and/or another device can convert the two recorded post-neuromodulation impedances to vessel diameters, and calculate a difference between the two vessel diameters.

It is expected that the baseline change in vessel impedance ($\Delta Zb$) or vessel diameter will be greater than the post-neuromodulation change vessel impedance ($\Delta Zn$) or vessel diameter when nerves have been ablated because the neural response to the stimulus has decreased. Accordingly, the method 200 can continue by comparing the difference of the baseline and post-neuromodulation vessel impedances (ΔZb−ΔZn) or vessel diameters to a predetermined threshold value indicative of a desired level of neuromodulation (decision block 250). As discussed above, the threshold may be equivalent to a percentage decrease in the change in vessel impedance/diameter or another predetermined value. In other embodiments, the method 200 does not measure the impedance values before each stimulus, and instead only measures the pre- and post-neuromodulation vessel impedances measured after each stimulus. In this embodiment, the pre- and post-neuromodulation impedance values, rather than the changes in these values, can be compared to each other to determine the efficacy of the neuromodulation therapy.

When the comparison of pre- and post-neuromodulation vessel impedances/diameters is greater than or equal to the predetermined threshold, the neuromodulation therapy is considered successful or effective, and the method 200 can end (block 250). However, if the difference between the pre- and post-neuromodulation vessel impedances/diameters is less than the predetermined threshold, the method 200 can continue by applying another round of neuromodulation energy to the treatment site (block 225). The second application of neuromodulation energy can be the equivalent in intensity and duration as the previous application of neuromodulation energy, or it can be increased in intensity or duration to increase the likelihood of effective neuromodulation. The change in post-neuromodulation vessel impedance/diameter can again be determined after the second application of neuromodulation energy as set forth in blocks 230-245. This change in post-neuromodulation vessel impedance/diameter can subsequently be compared to the predetermined threshold value (decision block 250) to determine whether the second application of neuromodulation energy was effective. These steps (blocks 230-250) can continue until the post-neuromodulation vessel impedances/diameter is at least equal to the predetermined threshold. The comparison of the pre- and post-neuromodulation vessel impedances/diameters to the threshold value can be performed automatically (e.g., by a controller), or the values can be provided to the clinician to assess the efficacy of the treatment.

In various embodiments, a clinician may opt to reposition the catheter within the vessel to select another target site at which to apply neuromodulation energy. For example, if the first target site within the vessel did not result in adequate neuromodulation after one or more energy applications, the clinician may reposition the catheter proximally or distally along the length of the vessel to locate a site that may be better suited for neuromodulation (e.g., because the nerves are closer to the vessel). Alternatively or in addition, the clinician may relocate the catheter within the vessel after a successful neuromodulation therapy at the first target site to create a second target site, and ablate additional nerves. When the clinician repositions the catheter, the method 200 can be repeated from the beginning (i.e., block 205) so that the baseline vessel impedance/diameter is specific to the new target site.

Figure 3:
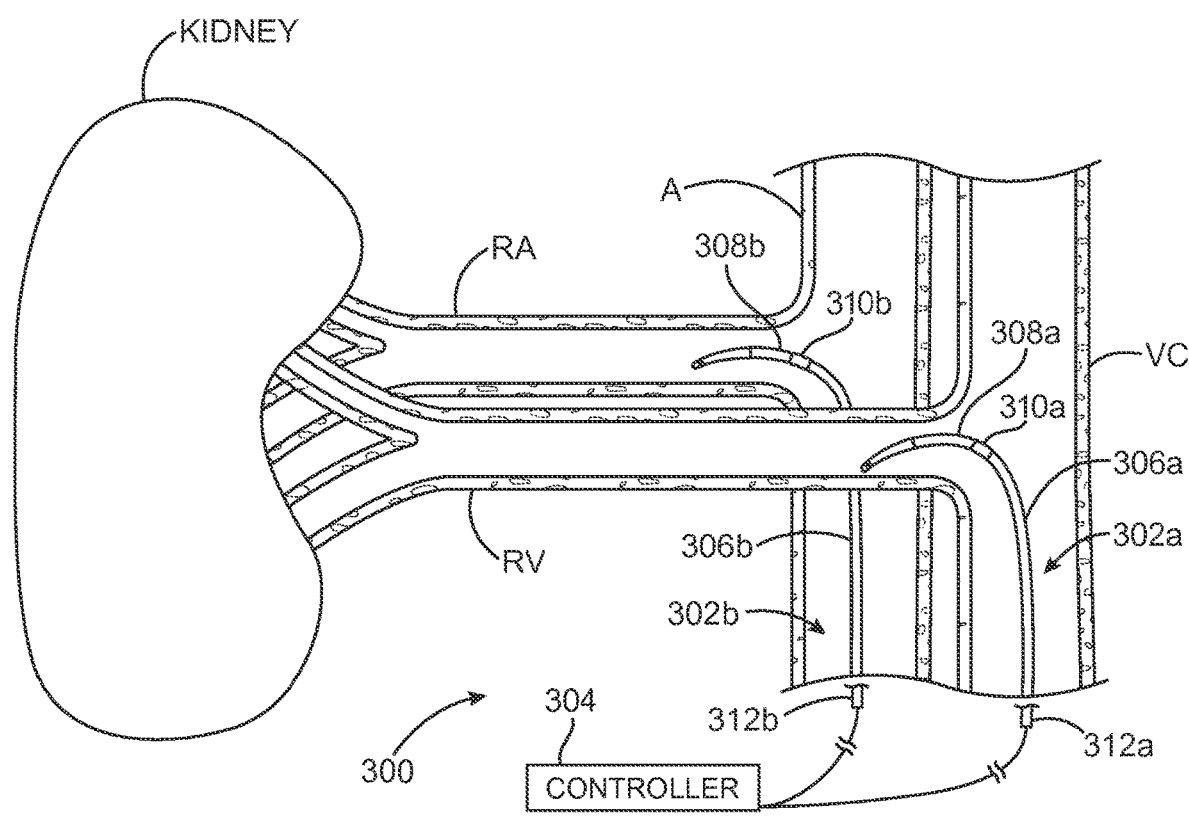
FIG. 3 is a partially schematic side view of a neuromodulation/evaluation system with distal portions of catheters positioned within a renal artery and a renal vein of a patient in accordance with an embodiment of the present technology.

FIG. 3 is a partially schematic side view of a system 300 for evaluating neuromodulation therapy ("system 300") configured in accordance with another embodiment of the present technology. The system 300 includes a first catheter 302a and a second catheter 302b (collectively referred to as "catheters 302") communicatively coupled to a controller 304 via a wired or wireless connection. Each catheter 302 can include an elongated shaft (identified individually as a first shaft 306a and a second shaft 306b, and referred to collectively as shafts 306) having a distal portion (identified individually as a first distal portion 308a and a second distal portion 308b, and referred to collectively as distal portions 308) and a proximal portion (identified individually as a first proximal portion 312a and a second proximal portion 312b, and referred to collectively as the proximal portions 312). The distal portions 308 of each shaft 306 can carry at least one energy delivery element, such as an electrode (identified individually as a first electrode 310a and a second electrode 310b, and referred to collectively as electrodes 310). In the embodiment illustrated in FIG. 3, each catheter 302 includes a single electrode 310, but in other embodiments one or both of the catheters 302 may include more than one electrode 310.

As shown in FIG. 3, the first and second catheters 302a and 302b can be advanced through the vena cava VC and the abdominal aorta A, respectively, such that the distal portions 308 of the catheters 302 are positioned within or proximate to a renal vein RV and renal artery RA, respectively, of a patient. For example, in certain embodiments the first distal portion 308a of the first catheter 302a is positioned proximate to the ostium of the renal vein RV, and/or the second distal portion 308b of the second catheter 302b is positioned proximate to the ostium of the renal artery RA. In other embodiments, the distal portions 308 of the first and second catheters 302a and 302b are positioned completely within the renal vein RV and renal artery RA.

The system 300 can be configured to measure the impedance across the renal vein RV and the renal artery RA before and after neuromodulation therapy to assess the efficacy of the neuromodulation therapy. For example, before applying neuromodulation energy to a target site (e.g., within the renal artery RA), the first and second electrodes 310a and 310b can apply a stimulus across the renal vein RV and the renal artery RA, and then the same first and second electrodes 310a and 310b can be used to detect a baseline, pre-neuromodulation impedance across the renal artery and vein RA and RV resulting from the stimulus. In other embodiments, the catheters 302 can include multiple electrodes with at least one electrode designated to apply stimuli and at least another electrode designated to measure impedance. In further embodiments, the catheters 302 can be configured to apply pharmacological stimuli (e.g., similar to the catheter 102 of FIGS. 1A and 1B). The baseline, pre-neuromodulation impedance value represents the impedance across the renal perfusion bed before neuromodulation. That is, when impedance is taken across the renal artery RA and the renal vein RV, the impedance measurement is influenced, in large part, by the amount of blood perfusing the kidney because the measured field includes a low impedance path that extends from the renal artery RA, through the vasculature of the kidney, to the renal vein RV. In certain embodiments, the baseline, pre-neuromodulation impedance is equivalent to the difference between the impedances measured before and after stimulation.

After determining the baseline, pre-neuromodulation impedance, neuromodulation energy can be applied to a target site within the renal artery RA and/or renal vein RV. Similar to the application of neuromodulation energy described above, neuromodulation can be provided in the form of RF energy, pulsed energy, microwave energy, optical energy, ultrasound energy (e.g., intravascularly delivered ultrasound, extracorporeal ultrasound, and/or HIFU), direct heat energy, radiation, cryogenic cooling, chemical-based treatment, and/or another suitable type of neuromodulation means. In certain embodiments, for example, the second electrode 310b of the second catheter 302b can be used to apply neuromodulation energy (e.g., RF energy) to one or more target sites within the renal artery RA. In other embodiments, the first distal portion 308a of the first catheter 302a and/or the second distal portion 308b of the second catheter 302b can include multiple electrodes (e.g., similar to the spiral/helical catheter 102 illustrated in FIG. 1B) that deliver neuromodulation energy to one or more target sites.

After neuromodulation energy has been applied, the first and second electrodes 310a and 310b can apply a stimulus across the renal vein RV and the renal artery RA, and then the same first and second electrodes 310a and 310b can detect the resultant post-neuromodulation impedance across the renal artery RA and renal vein RV. In other embodiments, the post-neuromodulation impedance is determined by taking the difference between (1) the impedance measured after neuromodulation, but before stimulation, and (2) the impedance measured after neuromodulation and after stimulation. The controller 304 can compare the baseline, pre-neuromodulation impedance value with the post-neuromodulation impedance value to a predetermined threshold that is indicative of successful ablation. It is expected that successful neuromodulation will increase renal perfusion and, accordingly, blood volume within the kidney. Therefore, post-neuromodulation impedance is expected to be lower than the pre-neuromodulation baseline impedance. Accordingly, the threshold value may be a predetermined decrease in the impedance value (e.g., 10%, 20%, 30%, 40%, etc. less than the pre-neuromodulation impedance value) and/or another suitable value associated with effective neuromodulation. If the difference between the pre-neuromodulation and post-neuromodulation impedances is at least equal to the predetermined threshold, the neuromodulation therapy may be deemed successful in ablating nerves to the desired degree, whereas if the difference is less than a predetermined threshold, the clinician may opt to apply additional rounds of neuromodulation energy at the treatment site or at another treatment site along the vessel. Accordingly, like the system 100 described above with reference to FIGS. 1A and 1B, the system 300 of FIG. 3 can provide a user with feedback as to the effectiveness of neuromodulation therapy. Additionally, in embodiments in which one or both of the catheters 302 are configured to deliver neuromodulation therapy, the system 300 can provide feedback to clinicians regarding the efficacy of neuromodulation treatments in substantially real time, and therefore allows clinicians to apply additional rounds of neuromodulation therapy without needing to reinsert the neuromodulation catheter(s) 302 into the patient.

Figure 4:
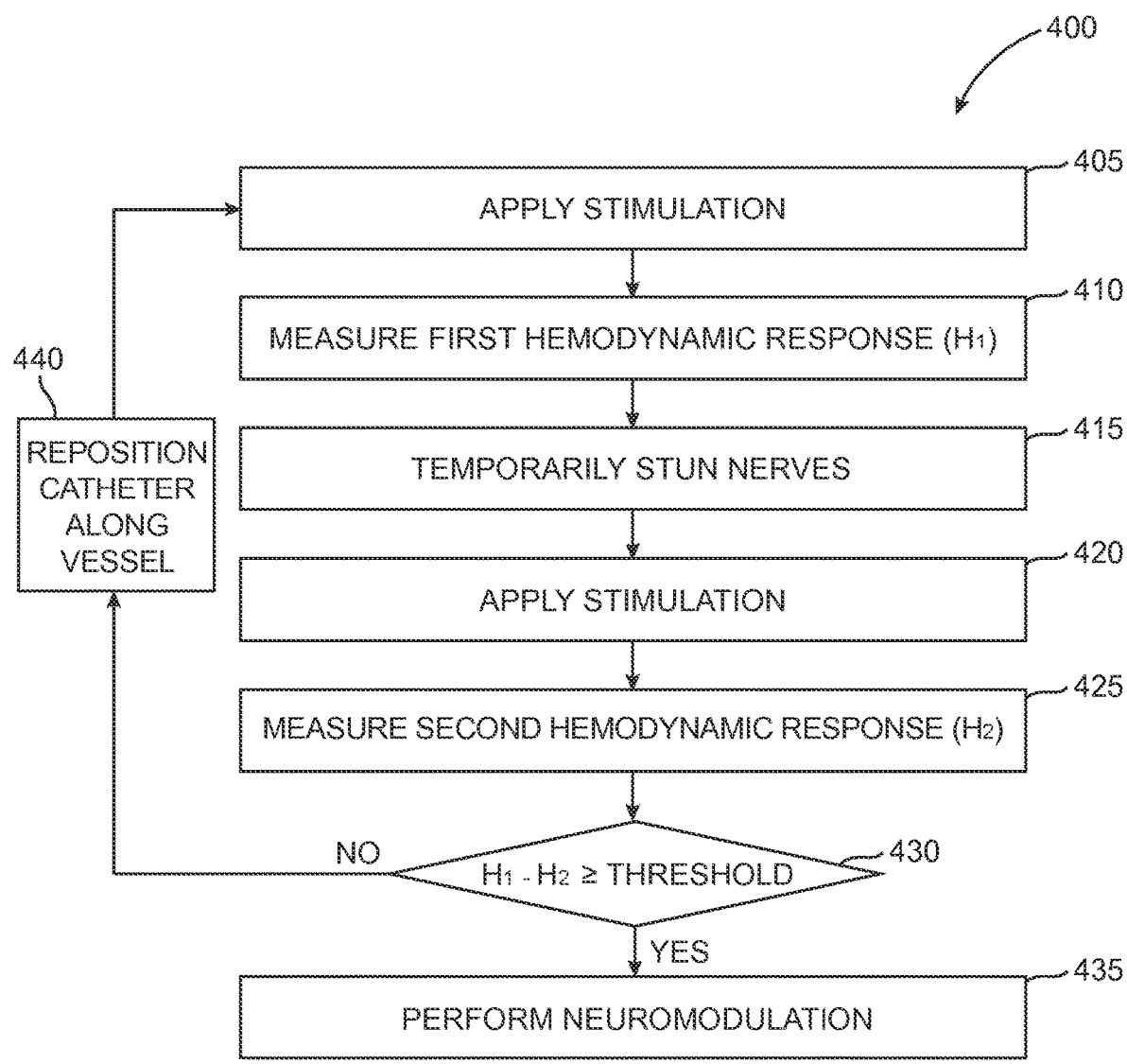
FIG. 4 is a block diagram illustrating a method of determining a treatment site within a blood vessel in accordance with an embodiment of the present technology.

FIG. 4 is a block diagram illustrating a method 400 of determining a treatment site within a blood vessel in accordance with an embodiment of the present technology. The method 400 can be performed using the systems 100 and 300 described above with respect to FIGS. 1A, 1B, and 3, or using other suitable systems. After a distal portion of a catheter is positioned at a potential treatment site within a vessel, the method 400 can begin by applying a first stimulus at the treatment site (block 405), and measuring a first hemodynamic response ($H_1$) to the first stimulus (block 410). The first stimulus can be an electrical stimulus and/or a pharmacological stimulus sufficient to stimulate nerves proximate to a treatment site. For example, an electrical stimulus can be applied via one or more electrodes at a distal portion of a catheter positioned proximate to or within a vessel, such as a renal artery. The electrode(s) may contact the vessel wall when delivering the stimulus, or the electrode(s) may be spaced apart from the vessel wall (e.g., as shown in FIG. 1A). Alternatively, a catheter can deliver a pharmacological agent into the vessel or inject the pharmacological agent into the vessel wall to acutely stimulate nerves proximate to the vessel. The first hemodynamic response ($H_1$) can correspond to blood flow through the vessel, pressure within the vessel, vessel impedance, vessel diameter, impedance across a perfusion bed (e.g., across the renal artery and renal vein), and/or other hemodynamic parameters affected by stimuli. The first hemodynamic response ($H_1$) can refer to a hemodynamic parameter derived from the difference between a baseline, pre-stimulus hemodynamic measurement and a post-stimulus hemodynamic measurement. In other embodiments, the first hemodynamic response can simply refer to the measured response to the first stimulus. The first hemodynamic response ($H_1$) can be measured via sensors, electrodes, and/or other features at the distal portion of the catheter. For example, the catheter can include a blood flow sensor to determine the blood flow within the vessel in response to the first stimulus and/or a pressure sensor to detect pressure within the vessel in response to the first stimulus.

As shown in FIG. 4, the method 400 can continue by temporarily stunning nerves at the treatment site (block 415). Temporarily stunning nerves can refer to temporarily preventing neural transmission or depolarization without permanent damage to the nerve. For example, nerves can be temporarily stunned by applying cryogenic cooling cold enough to stop neural transmission without permanent damage. This can be performed using a cryo-catheter at higher output temperatures and/or shorter lengths of time than the parameters used to create a lesion and/or permanently modulate nerves. In other embodiments, the nerves can be temporarily stunned by applying heat or electrical stimulation (e.g., via electrodes) to a vessel wall. For example, nerves can be temporarily stunned by applying RF energy to a vessel wall with electrodes positioned on a distal portion of a catheter (e.g., the helical catheter 102 illustrated in FIG. 1B). Accordingly, nerves can be temporarily stunned by applying higher energy or more cooling than required for the stimuli that evoke a hemodynamic response, but less energy or cooling than necessary to permanently modulate nerves.

While the nerves are temporarily stunned, a second stimulus can be applied at the treatment site (block 420), and a second hemodynamic response ($H_2$) to the second stimulus can be measured (block 425). The second hemodynamic response ($H_2$) can refer to a change in a hemodynamic parameter derived from the difference between a post-stunning, pre-stimulus hemodynamic parameter and a post-stunning, post-stimulus hemodynamic parameter, or to the hemodynamic parameter detected in response to the second stimulus. When the first and second hemodynamic responses correlate to the change in the hemodynamic response caused by the first and second stimuli, respectively, the first hemodynamic response ($H_1$) is expected to be higher than the second hemodynamic response ($H_2$) because the stunned nerves do not respond to the second stimulus, or at least not to the same extent as the nerves prior to stunning. When the first and second hemodynamic responses correlate solely to the hemodynamic responses measured after the first and second stimuli, respectively, the first hemodynamic response ($H_1$) is expected to be higher than the second hemodynamic response ($H_2$) when the stimuli causes vasoconstriction (e.g., electrical stimuli), and lower than the second hemodynamic response ($H_2$) when the stimuli cause vasodilation (e.g., pharmacological stimuli).

The difference between the first and second hemodynamic responses ($H_1$–$H_2$) can be compared to a predetermined threshold value indicative of a suitable site for neuromodulation (decision block 430). In certain embodiments, for example, the threshold value may correlate to a predetermined change in the hemodynamic response or a percentage decrease in the hemodynamic response. For example, any decrease in the hemodynamic responses taken before and after temporary stunning may indicate that there are nerves proximate to the site that was temporarily stunned, and therefore it may be a suitable location for neuromodulation. Accordingly, if the difference between the first and second hemodynamic responses is above the threshold value, the method 400 continues by performing neuromodulation at the same site where the nerves were temporarily stunned (block 435). If the difference between the first and second hemodynamic responses is less than the threshold, then the clinician can reposition the catheter to a different potential treatment site (block 440), and repeat the method 400 again until the difference in hemodynamic responses is higher than the predetermined threshold. In various embodiments, a controller can provide signals to the catheter to automatically apply stimuli, record resultant hemodynamic responses, and apply energy to temporarily stun nerves. The controller may also be configured to automatically compare the hemodynamic responses and provide the clinician with feedback as to whether the predetermined threshold is met. The method 400 can therefore be used before neuromodulation therapies to detect locations within a vessel with sufficient neural activity to allow for effective neuromodulation therapy.

Figure 5:
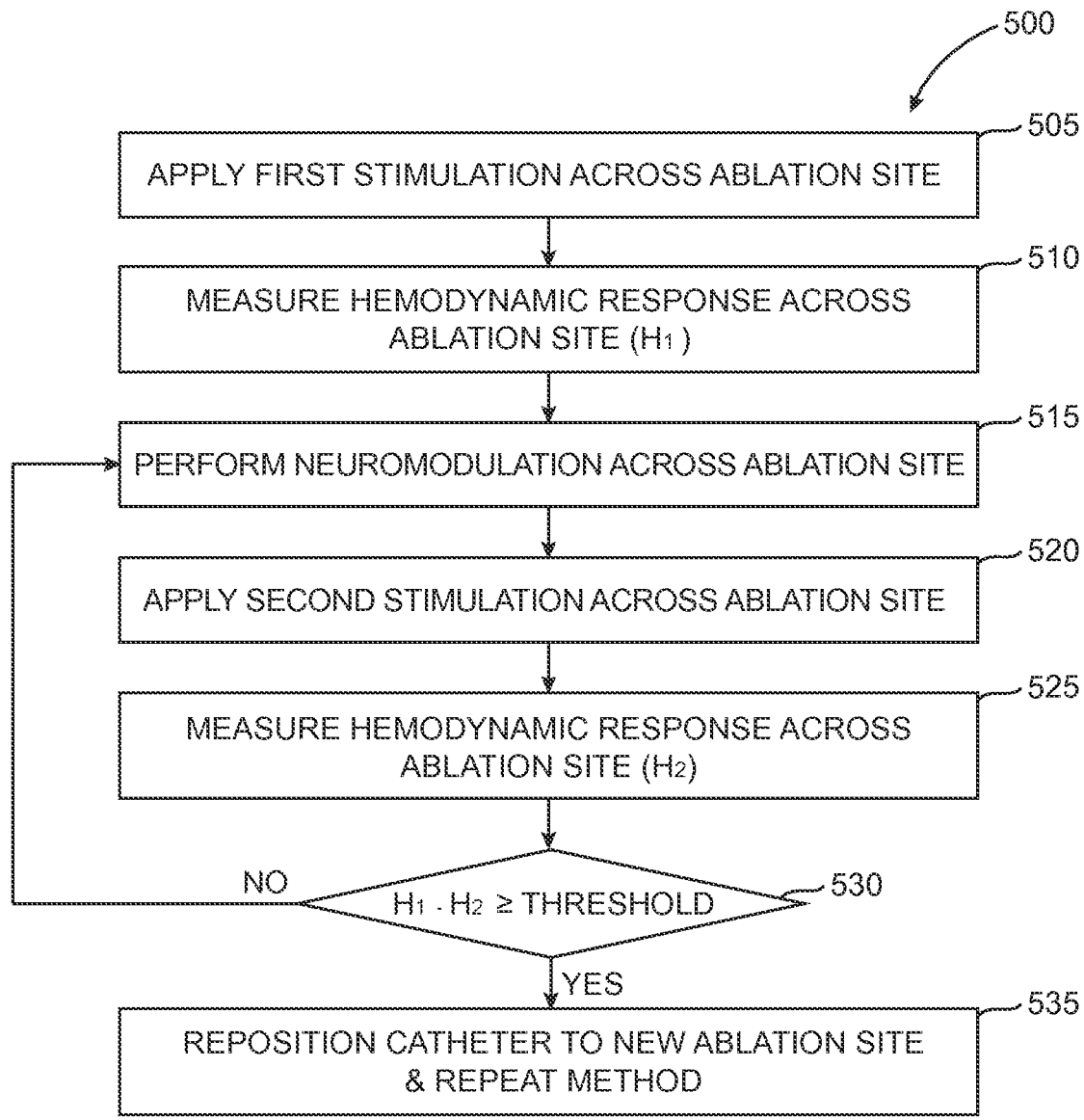
FIG. 5 is a block diagram illustrating a method of evaluating neuromodulation therapy at individual ablation sites in accordance with an embodiment of the present technology.

FIG. 5 is a block diagram illustrating a method 500 of evaluating neuromodulation therapy at individual ablation sites in accordance with an embodiment of the present technology. The method 500 can be performed using the system 100 described above with reference to FIGS. 1A and 1B and/or other suitable systems for evaluation neuromodulation therapy. As shown in FIG. 5, the method 500 includes applying a first stimulation across an ablation or treatment site (block 505), and measuring a first hemodynamic response ($H_1$) across the ablation site (block 510). The first hemodynamic response ($H_1$) can refer to a hemodynamic parameter detected in response to the first stimulus, or a change in a hemodynamic parameter derived from the difference between a pre-stimulus hemodynamic parameter and a post-stimulus hemodynamic parameter. In the method 500, the stimulus is applied locally to a specific ablation site, rather than globally across multiple ablation sites or along a larger length of a vessel. Accordingly, the stimulation applied may have a smaller amplitude than those stimulation pulses used to test global success of denervation (e.g., across an entire treatment site or along a larger portion of a vessel). For example, an electrical stimulus can be applied via electrodes on either side of the ablation site, and the hemodynamic response (e.g., blood flow, pressure, impedance, etc.) resulting from the local stimulation can be measured at or proximate to the ablation site.

The method 500 can continue by performing neuromodulation at the ablation site (block 515). The neuromodulation can be applied using the various forms of energy described above (e.g., RF energy), cryogenic cooling, and/or chemical-based treatment. After neuromodulation, a second stimulation can be applied across the ablation site (block 520), and a second hemodynamic response ($H_2$) can be measured across the ablation site (block 525). The second hemodynamic response ($H_2$) can refer to a hemodynamic parameter detected in response to the second stimulus, or a change in a hemodynamic parameter derived from the difference between a post-neuromodulation, pre-stimulus hemodynamic parameter and a post-neuromodulation, post-stimulus hemodynamic parameter.

The difference between the first and second hemodynamic responses ($H_1$–$H_2$) can be compared to a predetermined threshold (decision block 530). The predetermined threshold can be equal to a value indicative of successful neuromodulation across the ablation site. If the difference in the hemodynamic responses is lower than the predetermined threshold, the method can continue by reapplying neuromodulation energy across the ablation site and measuring the resultant hemodynamic response until it is higher than the threshold. When the difference between the first and second hemodynamic responses is at least equal to the threshold, the method 500 can continue by repositioning the catheter to a new ablation site 535 and repeating the method 500 at the new ablation site. The method 500 can be repeated until the clinician has performed neuromodulation at a desired number of ablation site.

The method 500 can be used to determine the effectiveness of neuromodulation across a specific ablation site. That is, the method 500 tests whether there is any neural tissue near an ablation site that will conduct a signal in response to a stimulus and evoke a hemodynamic response (e.g., pressure, blood flow, vessel diameter, etc.). If local stimulation indicates that the neuromodulation has been ineffective (i.e., block 530), then this information can be used by the clinician to apply additional rounds of neuromodulation therapy to the same ablation site to adequately modulate nerves at the ablation site.

Figure 6:
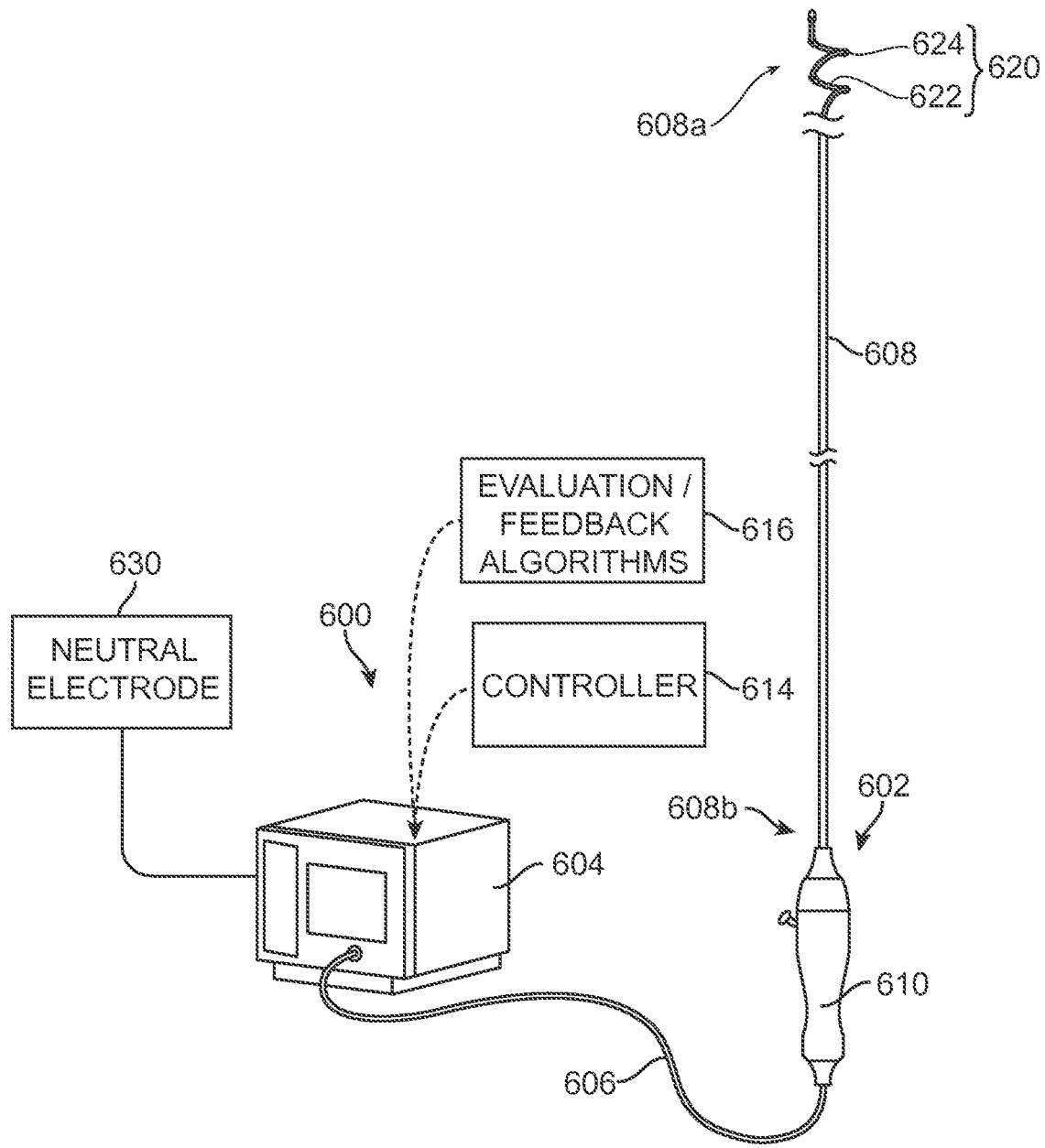
FIG. 6 is a partially schematic illustration of a neuromodulation system configured in accordance with another embodiment of the present technology.

FIG. 6 is a partially schematic illustration of a therapeutic system 600 ("system 600") configured in accordance with still another embodiment of the present technology. The system 600 can include various features similar to the systems 100 and 300 described above with respect to FIGS. 1A, 1B, and 3, and may be used to implement the various methods 200, 400, and 500 described above. As shown in FIG. 6, the system 600 includes a neuromodulation catheter 602, a console 604, and a cable 606 extending therebetween. The neuromodulation catheter 602 can include an elongated shaft 608 having a proximal portion 608b, a distal portion 608a, a handle 610 operably connected to the shaft 608 at the proximal portion 608b, and a neuromodulation assembly 620 operably connected to the shaft 608 at the distal portion 608a. The shaft 608 and the neuromodulation assembly 620 can be 2, 3, 4, 5, 6, or 7 French or another suitable size. As shown in FIG. 6, the neuromodulation assembly 620 can include a support structure 622 carrying an array of two or more electrodes 624. The electrodes 624 can be configured to apply electrical stimuli (e.g., RF energy) to target sites at or proximate to vessels within a patient, temporarily stun nerves, deliver neuromodulation energy to target sites, and/or detect vessel impedance. In various embodiments, certain electrodes 624 can be dedicated to applying stimuli and/or detecting impedance, and the neuromodulation assembly 620 can include other types of therapeutic elements that provide neuromodulation therapy using various modalities, such cryotherapeutic cooling, ultrasound energy, etc.

The distal portion 608a of the shaft 608 is configured to be moved within a lumen of a human patient and locate the neuromodulation assembly 620 at a target site within or otherwise proximate to the lumen. For example, shaft 608 can be configured to position the neuromodulation assembly 620 within a blood vessel, a duct, an airway, or another naturally occurring lumen within the human body. In certain embodiments, intravascular delivery of the neuromodulation assembly 620 includes percutaneously inserting a guide wire (not shown) into a body lumen of a patient and moving the shaft 608 and/or the neuromodulation assembly 620 along the guide wire until the neuromodulation assembly 620 reaches a target site (e.g., a renal artery). For example, the distal end of the neuromodulation assembly 620 may define a passageway for engaging the guide wire for delivery of the neuromodulation assembly 620 using over-the-wire (OTW) or rapid exchange (RX) techniques. In other embodiments, the neuromodulation catheter 602 can be a steerable or non-steerable device configured for use without a guide wire. In still other embodiments, the neuromodulation catheter 602 can be configured for delivery via a guide catheter or sheath (not shown).

Once at the target site, the neuromodulation assembly 620 can be configured to apply stimuli, detect resultant hemodynamic responses, and provide or facilitate neuromodulation therapy at the target site (e.g., using the electrodes 624 and/or other energy delivery elements). For example, the neuromodulation assembly 620 can detect vessel impedance via the electrodes 624, blood flow via a flow sensor (e.g., a Doppler velocity sensor), local blood pressure within the vessel via a pressure transducer or other pressure sensor, and/or other hemodynamic parameters. The detected hemodynamic responses can be transmitted to the console 604 and/or another device external to the patient. The console 604 can be configured to receive and store the recorded hemodynamic responses for further use by a clinician or operator. For example, a clinician can use the hemodynamic responses received by the console 604 to determine whether an application of neuromodulation energy was effective in modulating nerves to a desired degree.

The console 604 can be configured to control, monitor, supply, and/or otherwise support operation of the neuromodulation catheter 602. The console 604 can further be configured to generate a selected form and/or magnitude of energy for delivery to tissue at the target site via the neuromodulation assembly 620, and therefore the console 604 may have different configurations depending on the treatment modality of the neuromodulation catheter 602. For example, when the neuromodulation catheter 602 is configured for electrode-based, heat-element-based, or transducer-based treatment, the console 604 can include an energy generator (not shown) configured to generate RF energy (e.g., monopolar and/or bipolar RF energy), pulsed electrical energy, microwave energy, optical energy, ultrasound energy (e.g., intravascularly delivered ultrasound, extracorporeal ultrasound, and/or HIFU), direct heat energy, radiation (e.g., infrared, visible, and/or gamma radiation), and/or another suitable type of energy. When the neuromodulation catheter 602 is configured for cryotherapeutic treatment, the console 604 can include a refrigerant reservoir (not shown), and can be configured to supply the neuromodulation catheter 602 with refrigerant. Similarly, when the neuromodulation catheter 602 is configured for chemical-based treatment (e.g., drug infusion), the console 604 can include a chemical reservoir (not shown) and can be configured to supply the neuromodulation catheter 602 with one or more chemicals.

In selected embodiments, the system 600 may be configured to deliver a monopolar electric field via one or more of the electrodes 624. In such embodiments, a neutral or dispersive electrode 630 may be electrically connected to the console 604 and attached to the exterior of the patient. In embodiments including multiple electrodes 624, the electrodes 624 may deliver power independently (i.e., may be used in a monopolar fashion), either simultaneously, selectively, or sequentially, and/or may deliver power between any desired combination of the electrodes 624 (i.e., may be used in a bipolar fashion). In addition, an operator optionally may be permitted to choose which electrodes 624 are used for power delivery in order to form highly customized lesion(s) within the renal artery, as desired. One or more sensors (not shown), such as one or more temperature (e.g., thermocouple, thermistor, etc.), pressure, optical, flow, chemical, and/or other sensors, may be located proximate to, within, or integral with the electrodes 624. The sensor(s) and the electrodes 624 can be connected to one or more supply wires (not shown) that transmit signals from the sensor(s) and/or convey energy to the electrodes 624.

In various embodiments, the system 600 can further include a controller 614 communicatively coupled to the neuromodulation catheter 602. The controller 602 can be configured to initiate, terminate, and/or adjust operation of one or more components (e.g., the electrodes 624) of the neuromodulation catheter 602 directly and/or via the console 604. In other embodiments, the controller 614 can be omitted or have other suitable locations (e.g., within the handle 610, along the cable 606, etc.). The controller 614 can be configured to execute an automated control algorithm and/or to receive control instructions from an operator. Further, the console 604 can be configured to provide feedback to an operator before, during, and/or after a treatment procedure via an evaluation/feedback algorithm 616.

Figure 7:
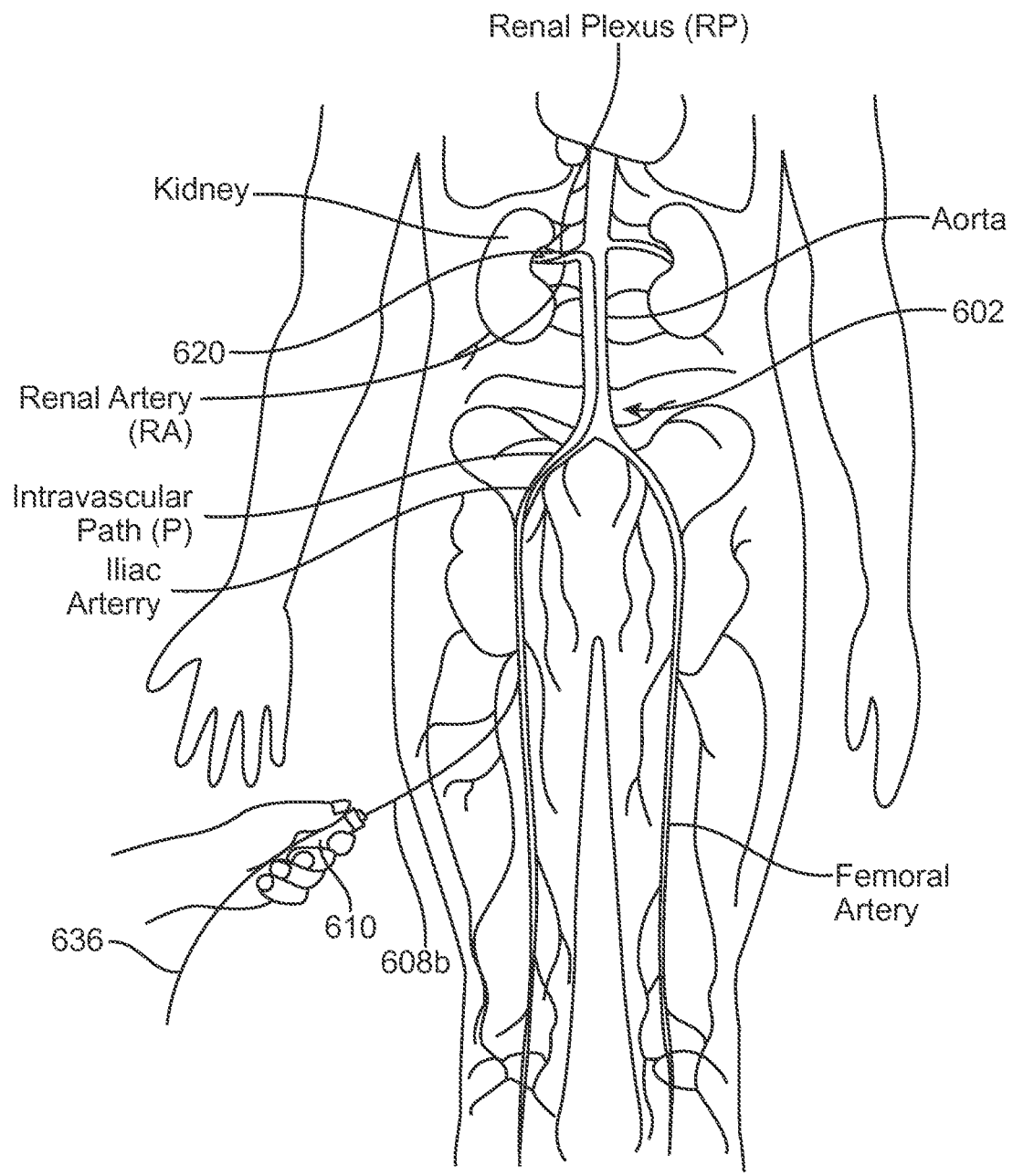
FIG. 7 illustrates modulating renal nerves and/or evaluating the neuromodulation therapy with the system of FIG. 6 in accordance with an embodiment of the present technology.

FIG. 7 (with additional reference to FIG. 6) illustrates modulating renal nerves in accordance with an embodiment of the system 600. The neuromodulation catheter 602 provides access to the renal plexus RP through an intravascular path P, such as a percutaneous access site in the femoral (illustrated), brachial, radial, or axillary artery to a targeted treatment site within a respective renal artery RA. By manipulating the proximal portion 608b of the shaft 608 from outside the intravascular path P, a clinician may advance the shaft 608 through the sometimes tortuous intravascular path P and remotely manipulate the distal portion 608a (FIG. 6) of the shaft 608. In the embodiment illustrated in FIG. 7, the neuromodulation assembly 620 is delivered intravascularly to the treatment site using a guide wire 636 in an OTW technique. As noted previously, the distal end of the neuromodulation assembly 620 may define a passageway for receiving the guide wire 636 for delivery of the neuromodulation catheter 602 using either OTW or RX techniques. At the treatment site, the guide wire 636 can be at least partially withdrawn or removed, and the neuromodulation assembly 620 can transform or otherwise be moved to a deployed arrangement for recording neural activity and/or delivering energy at the treatment site. In other embodiments, the neuromodulation assembly 620 may be delivered to the treatment site within a guide sheath (not shown) with or without using the guide wire 636. When the neuromodulation assembly 620 is at the target site, the guide sheath may be at least partially withdrawn or retracted and the neuromodulation assembly 620 can be transformed into the deployed arrangement. In still other embodiments, the shaft 608 may be steerable itself such that the neuromodulation assembly 620 may be delivered to the treatment site without the aid of the guide wire 636 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation assembly 620. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation assembly 620. Further, in some embodiments, image guidance components (e.g., IVUS, OCT) may be integrated with the neuromodulation catheter 602 and/or run in parallel with the neuromodulation catheter 602 to provide image guidance during positioning of the neuromodulation assembly 620. For example, image guidance components (e.g., IVUS or OCT) can be coupled to the neuromodulation assembly 620 to provide three-dimensional images of the vasculature proximate the target site to facilitate positioning or deploying the multi-electrode assembly within the target renal blood vessel.

Energy from the electrodes 624 (FIG. 6) and/or other energy delivery elements may then be applied to target tissue to induce one or more desired neuromodulating effects on localized regions of the renal artery RA and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

Hypothermic effects may also provide neuromodulation. For example, a cryotherapeutic applicator may be used to cool tissue at a target site to provide therapeutically-effective direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Embodiments of the present technology can include cooling a structure at or near an inner surface of a renal artery wall such that proximate (e.g., adjacent) tissue is effectively cooled to a depth where sympathetic renal nerves reside. For example, the cooling structure is cooled to the extent that it causes therapeutically effective, cryogenic renal-nerve modulation. Sufficiently cooling at least a portion of a sympathetic renal nerve is expected to slow or potentially block conduction of neural signals to produce a prolonged or permanent reduction in renal sympathetic activity.

The electrodes 624 and/or other features of the neuromodulation assembly 620 can intravascularly apply stimuli to the renal artery RA and detect hemodynamic responses to the stimuli before and/or after neuromodulation energy is applied to the renal artery RA. This information can then be used to determine the efficacy of the neuromodulation therapy. For example, the controller 614 (FIG. 6) can process the detected hemodynamic responses before and after neuromodulation and compare the change in hemodynamic response to a predetermined threshold to assess whether neuromodulation therapy was effective across the treatment site or at a specific ablation site.

II. RENAL NEUROMODULATION

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable target sites during a treatment procedure. The target site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a target site in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed electrical energy, microwave energy, optical energy, focused ultrasound energy (e.g., high-intensity focused ultrasound energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

III. RELATED ANATOMY AND PHYSIOLOGY

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

A. The Sympathetic Chain

Figure 8:
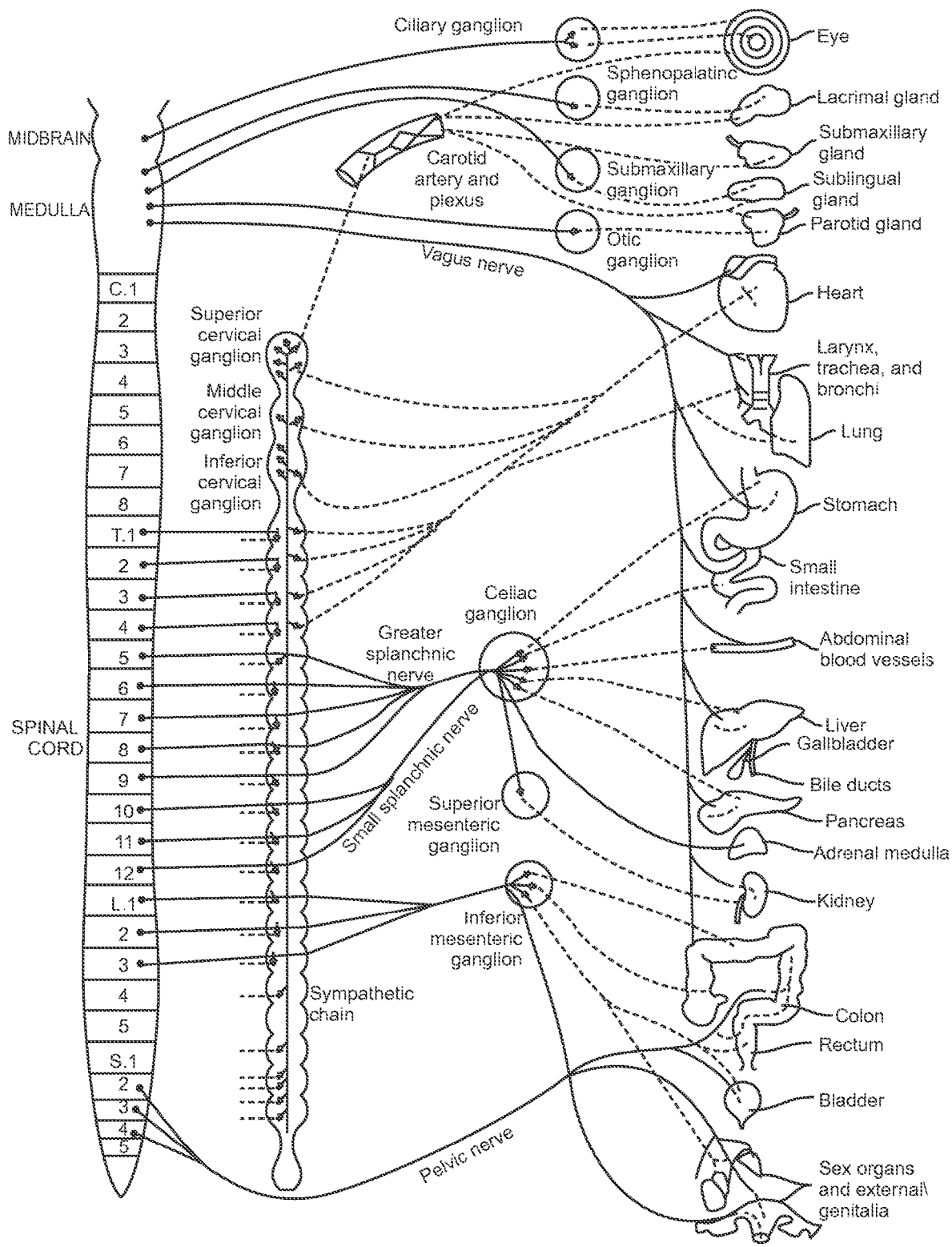
FIG. 8 is a conceptual illustration of the sympathetic nervous system (SNS) and how the brain communicates with the body via the SNS.

As shown in FIG. 8, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

1. Innervation of the Kidneys

Figure 9:
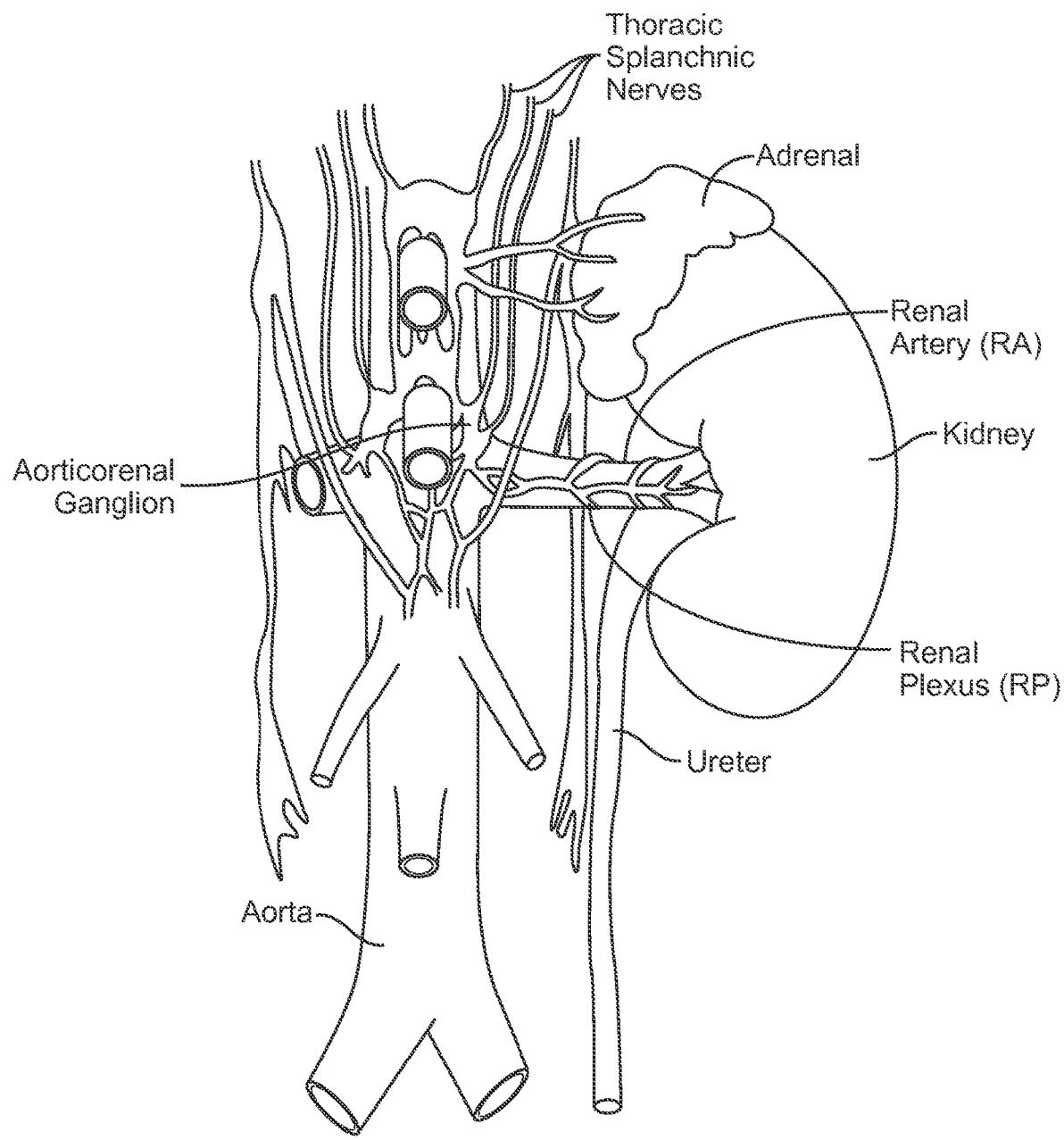
FIG. 9 is an enlarged anatomic view of nerves innervating a left kidney to form the renal plexus surrounding the left renal artery.

As FIG. 9 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

2. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 10:
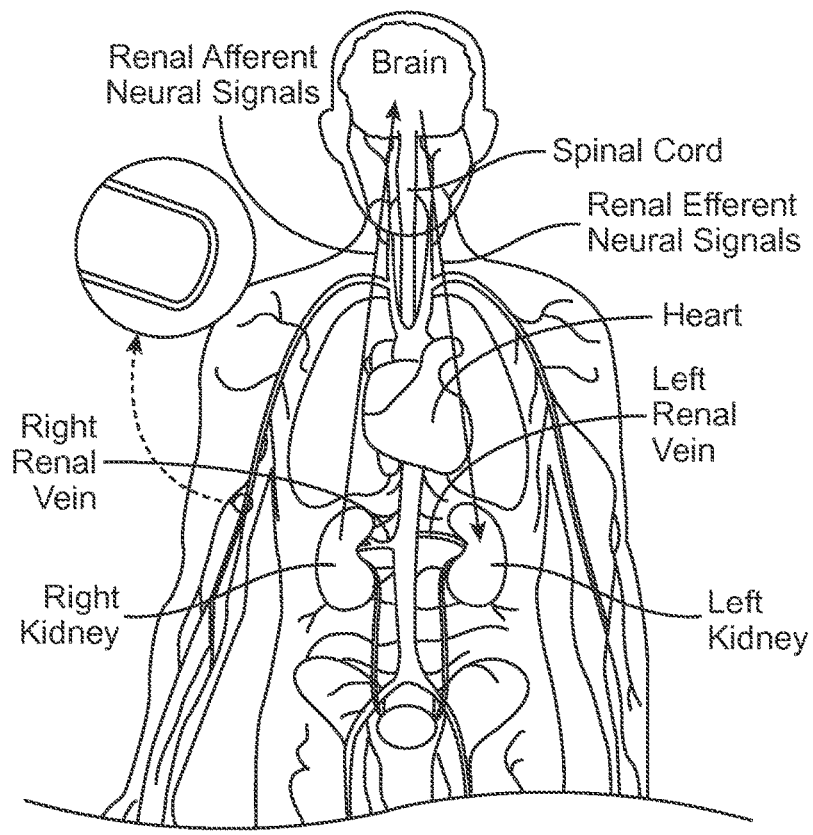
FIGS. 10 and 11 are anatomic and conceptual views, respectively, of a human body depicting neural efferent and afferent communication between the brain and kidneys.
Figure 11:
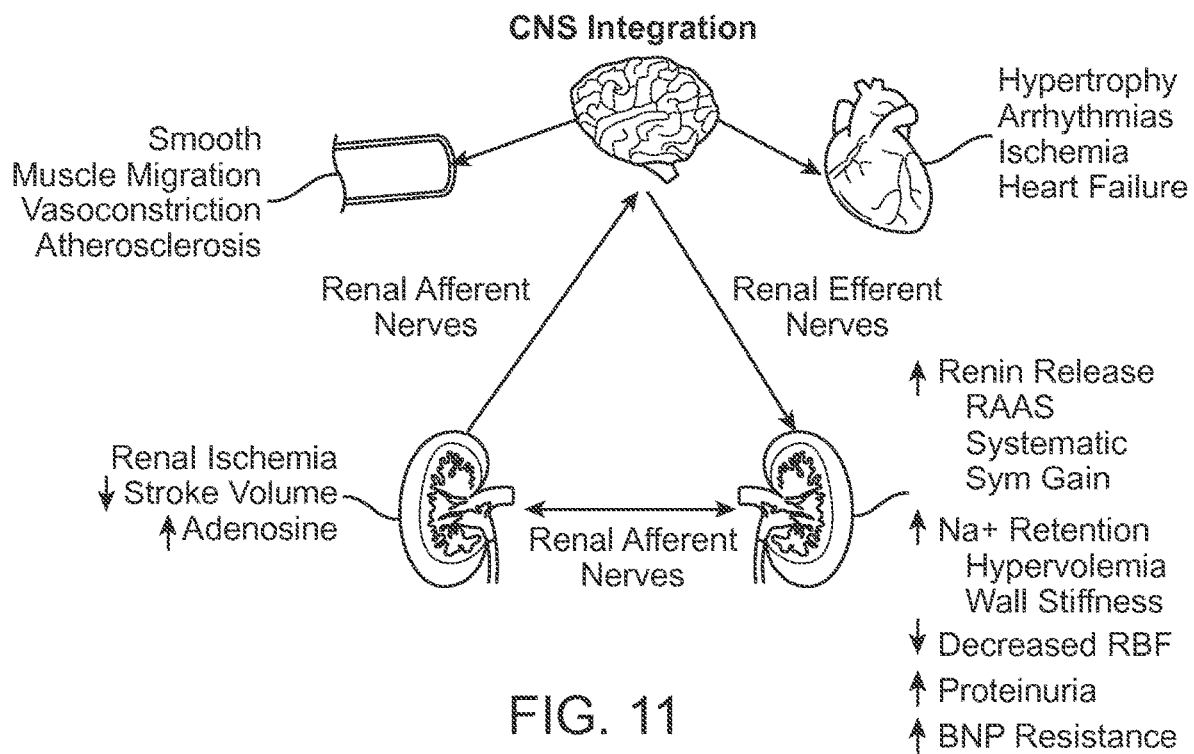

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 10 and 11, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 8. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 12:
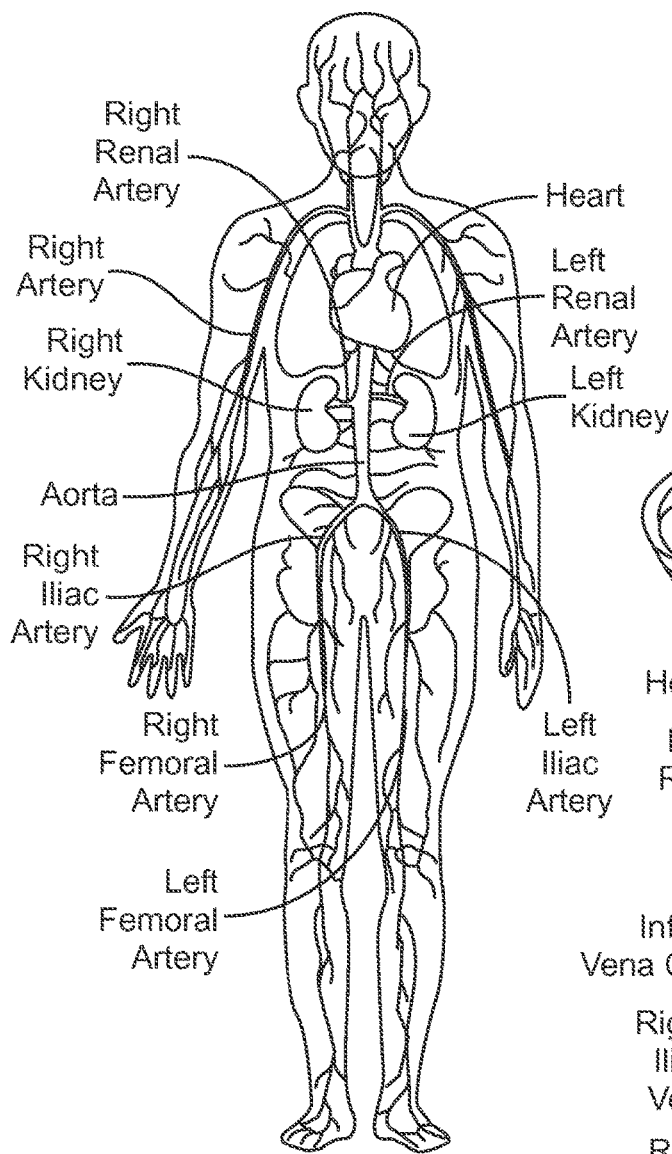
FIGS. 12 and 13 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 12 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 13:
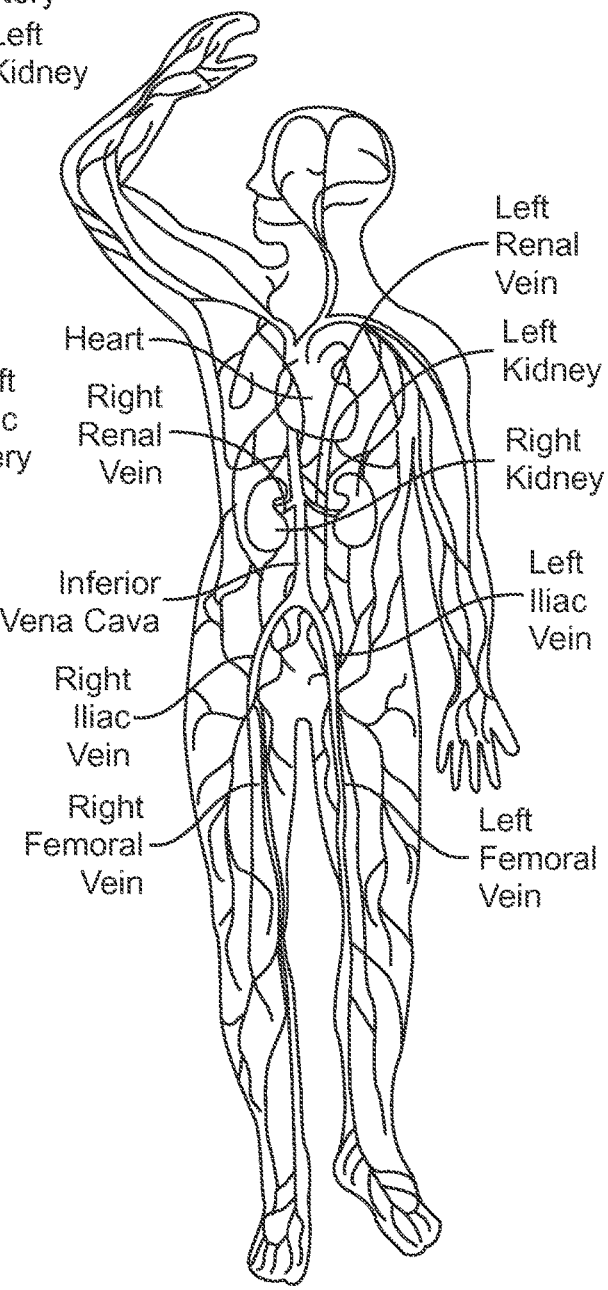

As FIG. 13 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications.

However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

IV. CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A method comprising:
    applying a first stimulus at a site within a blood vessel of a patient;
    determining a first hemodynamic response of the patient to the first stimulus;
    after the first stimulus is applied at the site, modulating activity of nerves at the site by non-ablative neuromodulation;
    after the activity of the nerves at the site is modulated, applying a second stimulus at the site;
    determining a second hemodynamic response of the patient to the second stimulus; and
    determining whether the site is a suitable location for neuromodulation therapy comprising denervation based on the first and second hemodynamic responses.

2. The method of claim 1, wherein the first stimulus comprises an electrical stimulus, and wherein applying the first stimulus comprises delivering the electrical stimulus via one or more electrodes of a catheter positioned within the blood vessel.

3. The method of claim 1, wherein applying the first stimulus comprises delivering a pharmacological agent into a wall of the blood vessel or into a lumen of the blood vessel.

4. The method of claim 1, wherein the first hemodynamic response corresponds to blood flow through the blood vessel, pressure within the blood vessel, a vessel impedance, a vessel diameter, a vessel cross-sectional area, a vessel segmental volume, or an impedance across a perfusion bed.

5. The method of claim 1, wherein determining the first hemodynamic response comprises sensing, via one or more sensors or electrodes, a patient parameter indicative of a response of the patient to the first stimulus.

6. The method of claim 5, wherein determining the first hemodynamic response further comprises determining a difference between a sensed value of the patient parameter and a predetermined value.

7. The method of claim 1, wherein modulating activity of nerves at the site comprises temporarily stunning the nerves, and wherein applying the second stimulus comprises applying the second stimulus while the nerves are temporarily stunned.

8. The method of claim 1, wherein modulating activity of nerves at the site comprises at least one of applying cryogenic cooling at the site, applying neuromodulation energy at the site, or delivering a chemical at the site.

9. The method of claim 1, wherein determining whether the site is the suitable location for neuromodulation therapy based on the first and second hemodynamic responses comprises:
   determining a difference between the first and second hemodynamic responses;
   determining the site is the suitable location for neuromodulation therapy in response to determining the difference is greater than or equal to a predetermined threshold; and
   determining the site is not the suitable location for neuromodulation therapy in response to determining the difference is less than the predetermined threshold.

10. The method of claim 1, wherein determining whether the site is a suitable location for neuromodulation therapy based on the first and second hemodynamic responses comprises determining that the site is the suitable location, the method further comprising, after determining the site is the suitable location for neuromodulation therapy, causing delivery of the neuromodulation therapy at the site within the blood vessel.

11. The method of claim 1, wherein determining whether the site is the suitable location for neuromodulation therapy comprises determining, by a controller, whether the site is the suitable location for neuromodulation therapy, the method further comprising:
   providing, by the controller, feedback to a user as to whether the site is the suitable location for neuromodulation therapy.

12. The method of claim 1, wherein the first hemodynamic response comprises a first hemodynamic parameter based on a difference between a pre-first stimulus hemodynamic measurement and a post-first stimulus hemodynamic measurement, and
   wherein the second hemodynamic response comprises a second hemodynamic parameter based on a difference between a pre-second stimulus hemodynamic measurement and a post-second stimulus hemodynamic measurement.

13. A system comprising:
   a controller configured to:
      determine a first hemodynamic response of a patient to a first stimulus applied at a site within a blood vessel of the patient;
      control a medical device to cause non-ablative modulation of activity of nerves at the site after the first stimulus is applied at the site;
      determine a second hemodynamic response of the patient to a second stimulus applied at the site after the activity of the nerves at the site is modulated; and
      determine whether the site is a suitable location for neuromodulation therapy comprising denervation based on the first and second hemodynamic responses.

14. The system of claim 13, further comprising a neuromodulation catheter configured to be positioned in the blood vessel, the neuromodulation catheter being configured to deliver the first and second stimuli to the site.

15. The system of claim 14, wherein the first stimulus comprises an electrical stimulus delivered via one or more electrodes of the neuromodulation catheter.

16. The system of claim 13, wherein the first stimulus comprises a pharmacological stimulus sufficient to stimulate nerves proximate the site.

17. The system of claim 13, wherein the first hemodynamic response corresponds to blood flow through the blood vessel, pressure within the blood vessel, a vessel impedance, a vessel diameter, a vessel cross-sectional area, a vessel segmental volume, or an impedance across a perfusion bed.

18. The system of claim 13, wherein the controller is configured to control the medical device to cause modulation of activity of the nerves at the site by at least controlling the medical device to cause temporary stunning of the nerves, and wherein the controller is configured to determine the second hemodynamic response of the patient to the second stimulus that is applied while the nerves are temporarily stunned.

19. The system of claim 13, further comprising a neuromodulation catheter configured to apply cryogenic cooling at the site to cause the modulation of activity of the nerves or to apply heat or energy at the site to cause the modulation of activity of the nerves.

20. The system of claim 13, wherein the controller is configured to determine whether the site is the suitable location for neuromodulation therapy based on the first and second hemodynamic responses by at least:
   determining a difference between the first and second hemodynamic responses;
   determining the site is the suitable location for neuromodulation therapy in response to determining the difference is greater than or equal to a predetermined threshold; and
   determining the site is not the suitable location for neuromodulation therapy in response to determining the difference is less than the predetermined threshold.

21. The system of claim 13, wherein the controller is configured to, in response to determining that the site is the suitable location, control the medical device to deliver the neuromodulation therapy at the site within the blood vessel.

22. The system of claim 13, wherein the controller is configured to provide feedback to a user as to whether the site is the suitable location for neuromodulation therapy.

23. The system of claim 13, wherein the controller is further configured to:
   determine the first hemodynamic response by at least determining a first hemodynamic parameter based on a difference between a pre-first stimulus hemodynamic measurement and a post-first stimulus hemodynamic measurement; and determine the second hemodynamic response by at least determining a second hemodynamic parameter based on a difference between a pre-second stimulus hemodynamic measurement and a post-second stimulus hemodynamic measurement.

24. A system comprising:

a controller configured to:

control a medical system to apply a first stimulus at a site within a blood vessel of a patient;

determine a first hemodynamic response of the patient to the first stimulus;

control the medical system to deliver at least one of neuromodulation energy, cryogenic cooling, or a chemical-based treatment to temporarily stun nerves at the site after the first stimulus is applied at the site;

control the medical system to apply a second stimulus at the site after the nerves at the site are temporarily stunned;

determine a second hemodynamic response of the patient to the second stimulus; and determine whether the site is a suitable location for neuromodulation therapy based on the first and second hemodynamic responses.

25. The system of claim 24, wherein the controller is configured to determine whether the site is the suitable location for neuromodulation therapy based on the first and second hemodynamic responses by at least:

determining a difference between the first and second hemodynamic responses;

determining the site is the suitable location for neuromodulation therapy in response to determining the difference is greater than or equal to a predetermined threshold; and determining the site is not the suitable location for neuromodulation therapy in response to determining the difference is less than the predetermined threshold.

* * * * *